(12) United States Patent
Camrud et al.

(10) Patent No.: US 6,485,510 B1
(45) Date of Patent: *Nov. 26, 2002

(54) MULTI-SECTION STENT

(75) Inventors: Allan R. Camrud, Rochester, MN (US); David R. Holmes, Jr., Rochester, MN (US); Robert S. Schwartz, Rochester, MN (US)

(73) Assignee: Mayo Foundation for Medical Education and Research, Rochester, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,681

(22) Filed: Apr. 14, 2000

Related U.S. Application Data

(63) Continuation-in-part of application No. 09/292,558, filed on Apr. 15, 1999, now Pat. No. 6,258,117.

(51) Int. Cl.[7] .................................................. A61F 2/06
(52) U.S. Cl. ...................................................... 623/1.16
(58) Field of Search .............................. 623/1.15, 1.16, 623/23.7, 1.28, 1.29, 1.38

(56) References Cited

U.S. PATENT DOCUMENTS

| | | | |
|---|---|---|---|
| 4,182,339 A | * 1/1980 | Hardy, Jr. .................. | 623/1.15 |
| 5,122,154 A | 6/1992 | Rhodes | |
| 5,441,515 A | 8/1995 | Khosravi et al. | |
| 5,562,697 A | 10/1996 | Christiansen | |
| 5,584,877 A | 12/1996 | Miyake et al. | |
| 5,591,197 A | 1/1997 | Orth et al. | |
| 5,591,223 A | 1/1997 | Lock et al. | |
| 5,723,003 A | 3/1998 | Winston et al. | |
| 5,725,567 A | 3/1998 | Wolff et al. | |
| 5,766,710 A | 6/1998 | Turnlund et al. | |
| 5,824,048 A | 10/1998 | Tuch | |
| 5,843,172 A | 12/1998 | Yan | |
| 5,873,904 A | 2/1999 | Ragheb et al. | |
| 5,957,975 A | * 9/1999 | Lafont et al. ............... | 623/1.38 |
| 6,022,359 A | 2/2000 | Frantzen | |
| 6,187,034 B1 | * 2/2001 | Frantzen .................... | 623/1.11 |
| 6,214,037 B1 | * 4/2001 | Mitchell et al. ............ | 623/1.11 |
| 6,258,117 B1 | * 7/2001 | Camrud et al. ............. | 623/1.16 |

FOREIGN PATENT DOCUMENTS

| | | | | |
|---|---|---|---|---|
| EP | 0 716 836 A1 | * 6/1996 | ................ | 623/1.15 |
| EP | 1 005 843 A2 | * 6/2000 | ................ | 623/1.15 |
| GB | 2 360 456 A | * 3/2000 | ................ | 623/1.15 |
| WO | WO 97/37617 | 10/1997 | | |
| WO | WO 00/15151 | 3/2000 | | |

* cited by examiner

Primary Examiner—David H. Willse
Assistant Examiner—Suzette J. Jackson
(74) Attorney, Agent, or Firm—Fish & Richardson, P.C., P.A.

(57) ABSTRACT

A stent includes a first stent section, a second stent section, and at least one connecting member. The connecting member has a first end attached to the first stent section, a second end attached to the second stent section and a physically separable portion.

20 Claims, 19 Drawing Sheets

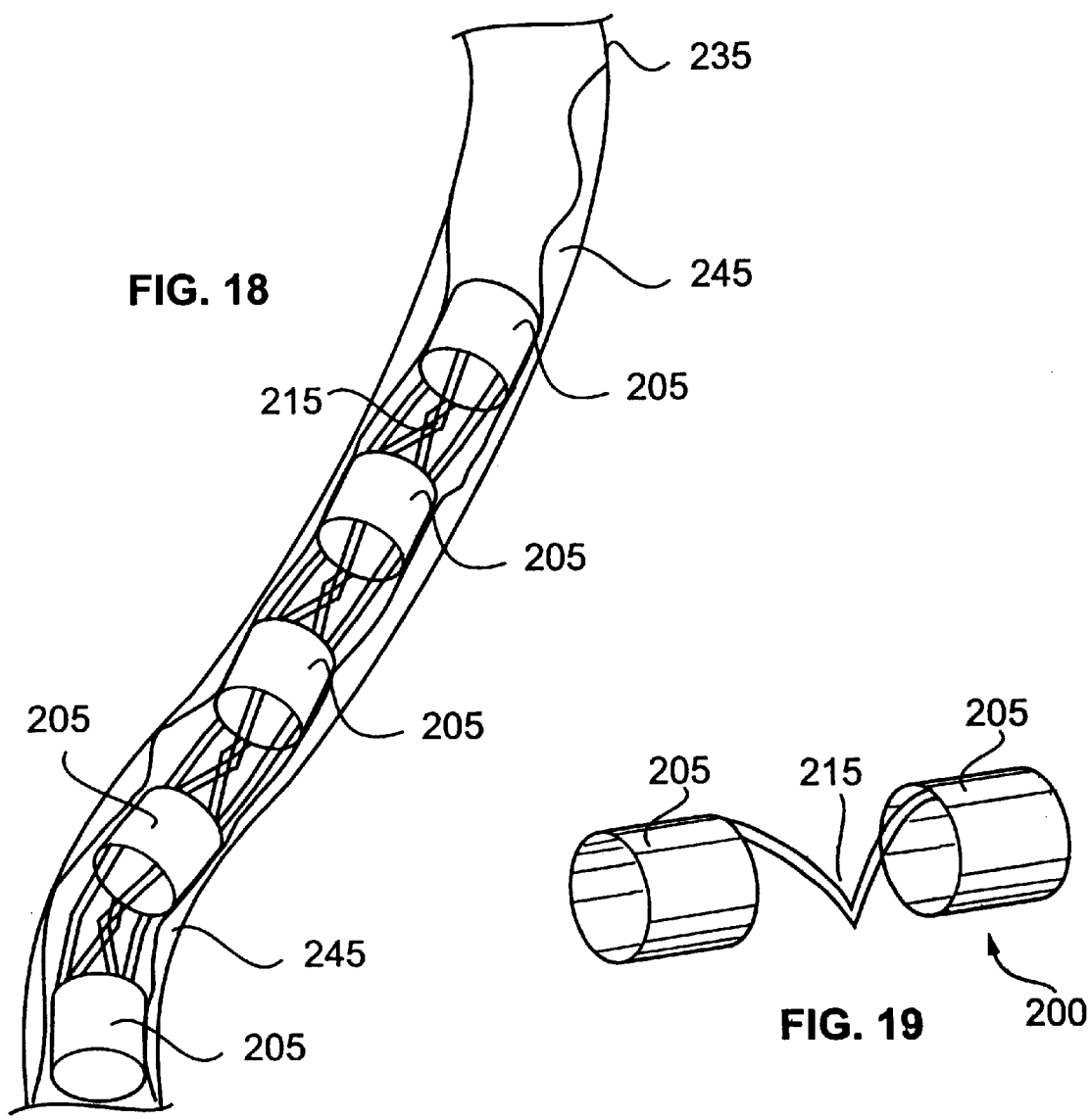
FIG. 18
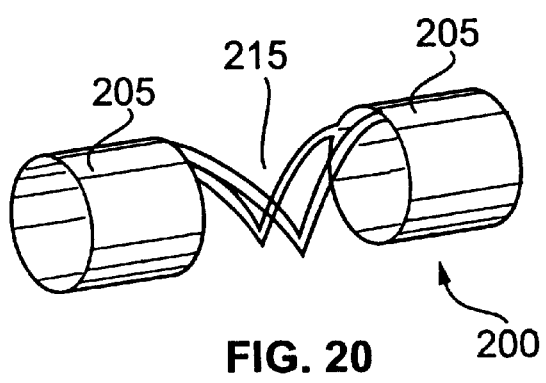
FIG. 19
FIG. 20

MULTI-SECTION STENT

This application is a continuation-in-part of U.S. Ser. No. 09/292,558, filed Apr. 15, 1999, now U.S. Pat. No. 6,258, 117.

TECHNICAL FIELD

The present invention relates to medical prostheses and, more particularly, to intraluminal medical stents.

BACKGROUND

Medical stents are used within the body to restore or maintain the patency of a body lumen. Blood vessels, for example, can become obstructed due to plaque or tumors that restrict the passage of blood. A stent typically has a tubular structure defining an inner channel that accommodates flow within the body lumen. The outer walls of the stent engage the inner walls of the body lumen. Positioning of a stent within an affected area can help prevent further occlusion of the body lumen and permit continued flow.

A stent typically is deployed by percutaneous insertion of a catheter or guide wire that carries the stent. The stent ordinarily has an expandable structure. Upon delivery to the desired site, the stent can be expanded with a balloon mounted on the catheter. Alternatively, the stent may have a biased or elastic structure that is held within a sheath or other restraint in a compressed state. The stent expands voluntarily when the restraint is removed. In either case, the walls of the stent expand to engage the inner wall of the body lumen, and generally fix the stent in a desired position.

SUMMARY

The present invention is directed to a multi-section stent. The stent incorporates a connecting structure that permits the multiple sections to move relative to another, promoting flexibility and conformance of the stent to a body lumen. For deployment and positioning, the connecting structure holds the stent sections substantially stationary relative to one another. Following deployment, however, the connecting structure allows the multiple stent sections to move relative to one another.

The connecting structure can be made to separate or relax such that the stent sections are able to move relative to one another. The connecting structure can be made to separate or relax by the use of a material that breaks or degrades. Movement of the stent sections may refer to axial movement, lateral movement, tilting, pivoting, rotation, and the like, all of which promote flexibility of the overall stent structure.

Movable stent sections enable flexure of the stent upon deployment within a body lumen. This flexing structure allows better conformance of the stent to the shape of the body lumen, and exerts less overall pressure against the lumen wall, reducing the potential for trauma. Following separation or relaxation of the connecting structure, the multiple stent sections may be completely detached from one another. Alternatively, the stent sections may remain partially connected in a manner that allows substantial independent movement.

The connecting structure can be manufactured to separate, e.g., by breakage, tearing, rupture, etc., thereby disconnecting at least portions of adjacent stent sections to allow increased flexibility. Alternatively, the separable connecting structure can be made from a degradable material that dissolves or otherwise degrades within the body lumen. As a further alternative, the connecting structure may connect the stent sections in a non-rigid manner, allowing movement while retaining interconnection between the stent sections. In any of the above cases, adjacent stent sections become more movable relative to one another, allowing the stent to flex and adapt to the body lumen. Each of the individual stent sections may settle into a substantially fixed position, however, and heal into the luminal wall.

A separable connecting structure can be made responsive to intra-luminal forces or external forces applied upon deployment. To promote separation by breakage, a continuous stent structure can be weakened, e.g., by thinning, perforation, scribing, or pre-stressing, at selected intervals along the length of the stent. Alternatively, discrete connecting members can be formed between stent sections to provide a series of connected stent sections. The connecting members are manufactured to separate under intraluminal forces, thereby disconnecting the stent sections. To promote early separation or breakage, the deployment technique may involve forcibly breaking at least some of the connecting members. In many cases, however, gradual separation or breakage under intraluminal forces will be sufficient.

A connecting structure incorporating a degradable material can be selected to dissolve within the body fluids present within the body lumen in which the stent is positioned. Early degradation can be promoted by pretreating the material, e.g., with a solvent, just prior to deployment. Also, an agent may be introduced into the body to accelerate degradation. If the connecting structure comprises a collagen coating, for example, an enzyme dosage can be administered to the patient to promote degradation. Gradual degradation will be sufficient in most applications, however, simplifying preparation. With degradable materials, therapeutic substances can be added for release into the body lumen as the materials degrade.

As an alternative, the stent can be covered with a brittle or degradable laminating coat that covers at least a portion of the stent, forming a housing for the stent sections. This housing can provide a substantially rigid but separable interconnection of the stent sections. Upon deployment, the housing breaks or degrades to permit greater flexibility among the stent sections. Another alternative is the use of a housing in the form of a breakable or degradable netting or cage that holds the sections together. Upon deployment, the netting or cage can be made to break or degrade, and thereby release the stent sections relative to one another.

Separable connecting portions, whether degradable or breakable, can be selected and manufactured to minimize the risk of releasing larger particles or fragments into the body lumen that could lead to embolism or other serious problems. The stent sections may be completely separated, i.e., disconnected, following breakage of the connecting structure, forming a series of discrete stent sections that extend along the body lumen. Alternatively, the stent sections may remain partially connected, but still provide improved flexibility. For example, material joining adjacent stent sections may remain partially intact to allow flexibility but limit movement.

As further alternatives, the stent sections can be connected with interlocking links, such as loops or chain-links, that allow the stent sections to move, but serve to restrict the overall extent of movement. In some embodiments, the interlocking links may overlap, with degradable or breakable material filling the overlap area to hold adjacent stent sections in a substantially fixed manner and at a substantially fixed distance relative to one another. Following degradation or breakage of the material in the overlap, the links allow at least some degree of movement of the stent sections. In this manner, the length of the stent may increase following deployment, and occupy a greater extent within the body lumen.

In one embodiment, the present invention provides a stent comprising a first stent section, a second stent section, and a connecting structure that connects the first and second stent sections, the connecting structure allowing the first and second stent sections to move relative to one another upon deployment of the stent within a body lumen.

In another embodiment, the present invention provides a stent comprising a first stent section, a second stent section, a first link extending from the first stent section, a second link extending from the second stent section, wherein the first and second links interlock and define an overlap region, and a material formed in the overlap region to hold the first and second stent sections in a substantially fixed relationship, wherein the material is separable upon deployment of the stent within a body lumen, thereby enabling the first and second stent sections to move relative to one another.

In a further embodiment, the present invention provides a stent comprising a first stent section, a second stent section, a first link that interlocks with a second link in the first stent section and a third link in the second stent sections, thereby connecting the first and second stent sections, wherein the first link defines a first overlap region with the second link and a second overlap region with the third link, and a material formed in the first and second overlap regions to hold the first and second stent sections in a substantially fixed relationship, wherein the material is separable upon deployment of the stent within a body lumen, thereby enabling the first and second stent sections to move relative to one another.

In an added embodiment, the present invention provides a stent comprising a first stent section, a second stent section, and a connecting member that connects the first and second stent sections, the connecting member holding the first and second stent sections in a substantially fixed relationship, wherein the connecting member relaxes the connection between the first and second stent sections following deployment of the stent within a body lumen, thereby enabling flexure of the stent.

In another embodiment, the present invention provides a stent comprising a first stent section including a first spring coil, a second stent section including a second spring coil, a first spring arm extending from the first stent section, a second spring arm extending from the second stent section, and a material that connects the first and second spring arms, the material being breakable, thereby at least partially disconnecting the first and second stent sections and allowing the first and second stent sections to move relative to one another.

In a further embodiment, the present invention provides a stent comprising a first stent section, a second stent section, and a housing that encloses at least portions of the first and second stent sections, wherein the housing is breakable upon deployment, thereby allowing the stent sections to move relative to one another following degradation of the housing.

In another embodiment, the present invention provides a stent comprising a first stent section, a second stent section, and a housing that encloses at least portions of the first and second stent sections, wherein the housing is degradable upon deployment, thereby allowing the stent sections to move relative to one another following degradation of the housing.

In another embodiment, the present invention provides a stent comprising a first stent section, a second stent section, and at least one connecting member having a first end attached to the first stent section, a second end attached to the second stent section and a physically separable portion. The physically separable portion may comprise at least one groove in the connecting member. The groove may be formed adjacent to the first end, or adjacent to the first end and the second end.

The connecting member of the stent may further include an angled portion. The angled portion may include a groove and the physically separable portion may comprise the groove. The angle may be less than 45°, between 45° and 135°, and/or between 135° and 180°.

The stent may include one, two, three, four, or more connecting members. If there are two connecting members, each connecting member may include a first end attached to the first stent section and a second end attached to the second stent section, and the first end of the first stent is adjacent to the first end of the second stent. The first end of the first connecting member and the first end of the second connecting member may be separated by approximately 180°. The second end of the first connecting member and the second end of the second connecting member may be separated by approximately 180°. In the stent, the physically separable portion may separate during a deployment of the stent or after a deployment of the stent.

In another embodiment, the stent includes a first stent section, a second stent section; and a pair of connecting members. The connecting members are positioned between the stent sections and connect the stent sections. Each connecting member is substantially coplanar over a portion of a length of the connecting member with the at least one stent section and includes a first end attached to the first stent section, a second end attached to the second stent section and a physically separable portion.

In the stent, the physically separable portion of a first connecting member may be configured to separate from the first stent section and the physically separable portion of the second connecting member may be configured to separate from the second stent section, whereby the first connecting member is configured to reduce tumbling of the first stent section and the second connecting member is configured to reduce tumbling of the second stent section. The stent may be fabricated by electron discharge machining.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 18 is a side view of a multi-sectional stent deployed in a non-tortuous artery having severe lesions;

FIG. 19 is a side view of a multi-sectional stent having one connecting member;

FIG. 20 is a side view of a multi-sectional stent having two connecting members;

Like reference numbers and designations in the various drawings indicate like elements.

DETAILED DESCRIPTION

Figure 1A:
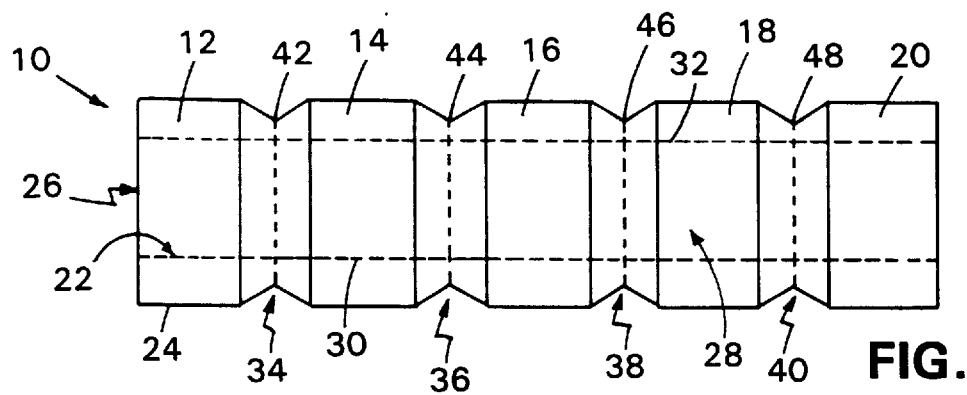
FIGS. 1A and 1B are side views of a multi-section stent having a separable connection structure incorporating v-shaped grooves.
Figure 1B:
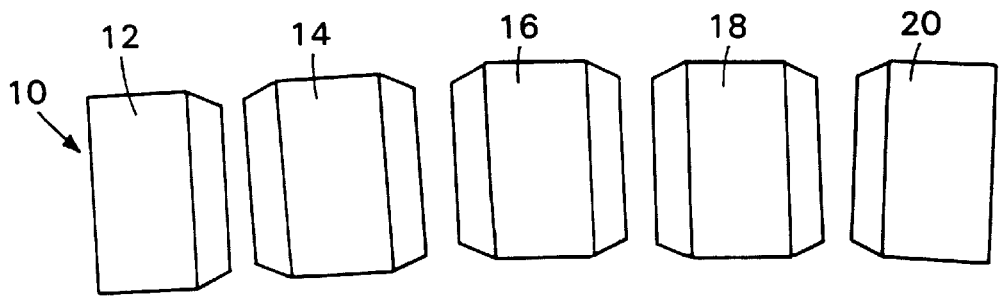
Figure 1C:
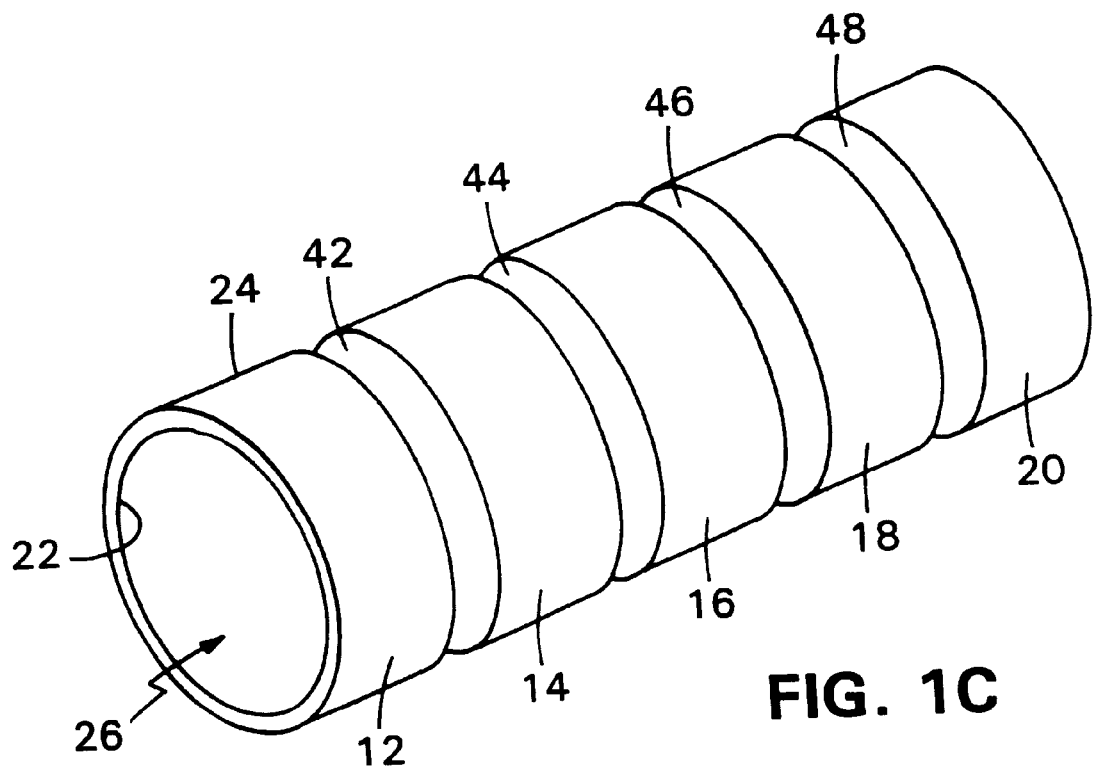
FIG. 1C is a perspective view of a multi-section stent as shown in FIG. 1A.

FIGS. 1A and 1B are side views of a multi-section stent 10 having a separable connection structure that facilitates enhanced flexibility. FIG. 1C is a perspective view of multi-section stent 10. In the example of FIGS. 1A–1C, multi-section stent 10 includes five stent sections 12, 14, 16, 18, 20. Stent 10 may include a lesser or greater number of stent sections, however, depending on the application. For example, stent 10 may include as few as two stent sections in some applications. Each stent section 12, 14, 16, 18, 20 has a ring-like structure with an inner wall 22, an outer wall 24, and a central aperture 26. Stent sections 12, 14, 16, 18, 20 are arranged coaxially and in series to form the longitudinal extent of stent 10. Stent sections 12, 14, 16, 18, 20 define an inner channel 28, indicated by dashed lines 30, 32 in FIG. 1A, that extends along the length of stent 10.

Upon deployment, inner channel 28 is sized to accommodate flow within a body lumen. Outer wall 24 of each stent section 12, 14, 16, 18, 20 is sized, upon deployment, to engage the inner surface of the body lumen, and thereby resist further occlusion. In this manner, stent 10 is effective in restoring or maintaining the patency of a body lumen, such as a blood vessel. The dimensions of stent sections 12, 14, 16, 18, 20 may vary depending on the application. In many applications, the diameters of inner wall 22 and outer wall 24 will be the same for all stent sections 12, 14, 16, 18, 20. Similarly, each of stent sections 12, 14, 16, 28, 20 may have the same axial length. For some applications, however, variation in the inner and outer diameters and lengths of individual stent sections 12, 14, 16, 18, 20 is conceivable.

Connecting members 34, 36, 38, 40 connect adjacent stent sections 12, 14, 16, 18, 20 to one another in a substantially fixed relationship. Connecting member 34, for example, forms a connection between adjacent stent sections 12 and 14. In the example shown in FIGS. 1A–1C, connecting members 34, 36, 38, 40 are not discrete components. Instead, connecting members 34, 36, 38, 40 are formed integrally with the body of stent 10. Stent 10 can be formed as a continuous structure, e.g., by molding, casting, lamination, deposition, or other known manufacturing processes. Each connecting member 34, 36, 38, 40 can be formed by thinning, perforating, pre-stressing or otherwise weakening portions of stent 10 between adjacent stent sections 12, 14, 16, 18, 20.

As shown in FIG. 1A, for example, connecting members 28, 30, 32, 34 may take the form of v-shaped grooves 42, 44, 46, 48 that are spaced axially along the length of stent 10 between adjacent stent sections 12, 14, 16, 18, 20. Each groove 42, 44, 46, 48 extends circumferentially about stent 10. The minimum diameter of each groove 42, 44, 46, 48 is sized larger than that of inner channel 22, but significantly smaller than that of stent 10. In this manner, grooves 42, 44, 46, 48 produce a thinned area that serves to weaken, and promote breakage of, stent 10 at selected positions. In particular, grooves 42, 44, 46, 48 preferably are designed to promote breakage of stent 10 in response to intra-luminal forces, either immediately following deployment or over an extended period of time. Upon breakage, stent sections 12, 14, 16, 18, 20 are separable from one another.

Stent sections 12, 14, 16, 18, 20 can be coated or impregnated with therapeutic materials such as heparin. The materials can be selected to dissolve upon deployment within the body lumen. For example, the materials can be incorporated in body-soluble sugars that dissolve within a blood vessel. Alternatively, the materials can be dissolved in response to introduction of a dissolving agent into the body. Collagen coatings, for example, can be selected to dissolve upon ingestion or injection of a particular enzyme dosage. As a further alternative, temperature-sensitive materials can be selected for coating or impregnation in stent sections 12, 14, 16, 18, 20. When heated to body temperature following deployment, the materials can dissolve to deliver desired therapeutic materials. Also, breakage could be further promoted by coating stent sections 12, 14, 16, 18, 20 with a material that swells upon absorption of fluid within the body lumen. Such a material could be selected to become more rigid upon absorption, thereby exerting a force against connecting members 34, 36, 38, 40 to induce breakage. Stent 10 can be constructed from a variety of different materials. Examples include metals such as gold, silver, platinum, stainless steel, tantalum, titanium, shape-memory alloys such as nickel-titanium alloys referred to as Nitinol, as well as synthetic polymers and biological materials such as natural fibrin. Such materials can be selected or coated to provide radio-opacity, if desired. Nitinol may be particularly advantageous in light of its memory properties. With Nitinol, stent 10 can be initially formed with a given configuration, and then deployed in a substantially flexible state. Stent 10 can be processed to provide connecting members 34, 36, 38, 40, which present weakened areas of the stent body. Upon deployment, the Nitinol can be heated, e.g., electrically or by exposure to body temperature, and thereby transformed to a more rigid state. In the process of transformation to a rigid state, the Nitinol exerts a force that promotes breakage of connecting members 34, 36, 38, 40.

In some embodiments, stent 10 can be formed by processing a substantially continuous starting material to provide connecting members 34, 36, 38, 40.

A substantially continuous, material can be formed by molding or casting. Grooves 42, 44, 46, 48 can be formed in initial manufacture or by subsequent processing. If stent 10 is formed by molding or casting, for example, grooves 42, 44, 46, 48 can be made during stent formation. Alternatively, the molding or casting operation may merely provide a blank for further processing. In this case, grooves 42, 44, 46, 48 can be formed, for example, by mechanical scribing, laser etching, chemically etching, or mechanical milling or lathing the stent to form the groove. As a further option, grooves 42, 44, 46, 48 could be thermally stamped or embossed, particularly if stent 10 is formed from a polymeric material. To further promote breakage, a series of perforations could be formed along grooves 42, 44, 46,48. In any event, grooves 42, 44, 46, 48 should be formed at a depth sufficient to promote breakage over time, but retain enough thickness to keep stent 10 substantially intact during deployment. Thus, determination of the depth of grooves 42, 44, 46, 48 may require a trade-off between ease of breakage and structural integrity during deployment.

The depths of grooves 42, 44, 46, 48, i.e., the degree of thinning of stent 10, can be the same. Stent sections 12, 14, 16, 18, 20 may be subject to different stresses due to their relative positioning along the length of stent 10, and the contour of the target site within the body lumen. As a result, some of connecting members 34, 36, 38, 40 may break more easily than others. Accordingly, for some applications, it may be desirable to form grooves 42, 44, 46, 48 with different depths to produce more uniform breakage characteristics despite different stresses existing at each connecting member 34, 36, 38, 40. Alternatively, other methods, such as perforation, pre-stressing, etching, scribing, milling, or lathing, may be used to weaken individual connecting members 34, 36, 38, 40 in a differential manner. Uniform breakage may be desirable for some applications, but does not imply that connecting members 34, 36, 38, 40 need to break at precisely the same time.

Upon breakage of stent 10 along grooves 42, 44, 46, 48, as shown in FIG. 1B, the adjacent stent sections 12, 14, 16, 18, 20 are disconnected and separate from one another. The disconnected stent sections 12, 14, 16, 18, 20 remain positioned proximate one another within the body lumen, but are able to move independently. Consequently, stent 10 maintains the patency of the body lumen while affording greater flexibility. In particular, depending on the contour and conditions of the target site, the disconnected stent sections 12, 14, 16, 18, 20 may be able to pivot, tilt, rotate, and move longitudinally within the body lumen relative to one another. Instead of presenting a rigid tube, stent 10 is better able to conform to the shape of the lumen.

Stent 10 ordinarily will be sized or biased such that the inner wall of the body lumen exerts significant force radially inward against outer wall 24. This radial force will tend to restrain stent sections 12, 14, 16, 18, 20 against excessive longitudinal movement. Given the radial force, outer wall 24 of each stent section 12, 14, 16, 18, 20 should have a surface area sufficient to prevent axial "tumbling" of the stent section, i.e, a collapse such that the circular cross-section of stent section moves away from a perpendicular position relative to the body lumen wall. If a stent section 12, 14, 16, 18, 20 is extremely short in length, relative to the longitudinal extent of the body lumen, tumbling can be a problem. With sufficient length, interaction between outer wall 24 and the inner wall of the body lumen will tend to anchor stent sections 12, 14, 16, 18, 20 against excessive movement. Eventually, stent sections 12, 14, 16, 18, 20 will settle into a generally stationary position and heal into the wall of the body lumen.

A separable connecting structure, as described herein, can be applied to a variety of different stent structures. Stent 10 can be fabricated from an elastomeric material or spring biased, for example, to allow compression for deployment. Instead of having a solid, or substantially continuous body, stent 10 can be fabricated by wrapping a sinusoidally shaped wire in a series of turns about a form to provide a tube-like shape. Adjacent wire turns can be partially cut or otherwise weakened to promote breakage at connecting members 34, 36, 38, 40. Upon release from a delivery catheter, sleeve, or other restraint, stent 10 is able to voluntarily expand radially outward to fill the body lumen. Stents of this type are often referred to as self-expandable.

As an alternative, stent 10 can have an assisted expansion structure. Expansion can be assisted, for example, by inflating a balloon disposed within the stent. Self-expandable and balloon-expandable stent structures are well known in the art. Optionally, the breakable connecting structure can be made to break upon expansion of the stent, thereby disconnecting the stent sections. As a further option, stent 10 may have a structure that enables the delivery of a variety of therapeutic substances to the body lumen. For example, stent 10 can be constructed with a mesh or cellular material loaded with one or more therapeutic substances that are released over time.

Figure 2A:
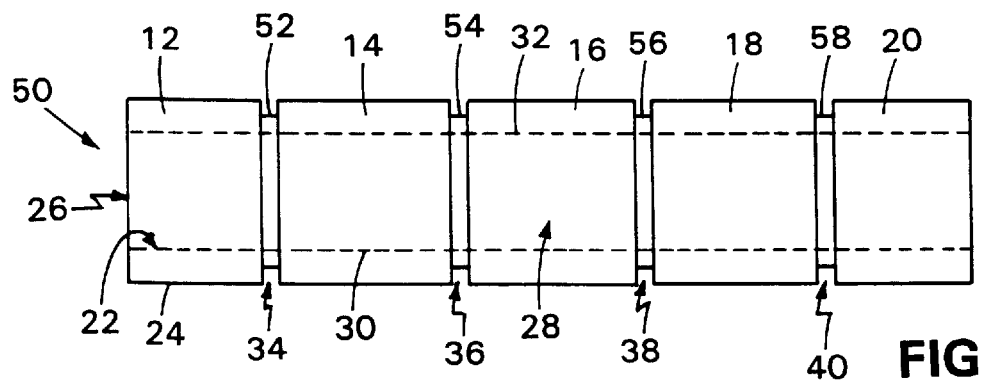
FIGS. 2A and 2B are side views of a multi-section stent having a separable connection structure incorporating square grooves.
Figure 2B:
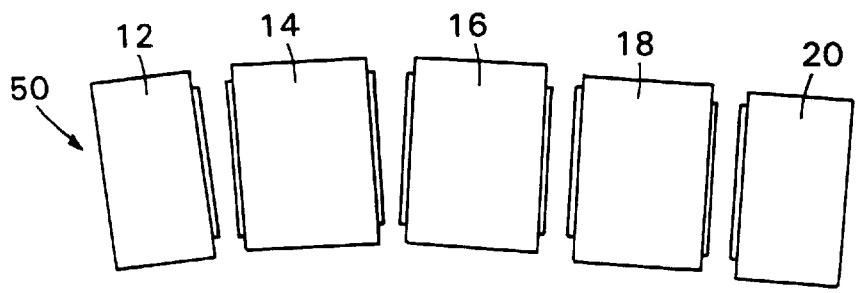

FIGS. 2A and 2B are side views of a multi-section stent 50 having a breakable connection structure incorporating square grooves 52, 56, 58, 60. Stent 50 substantially conforms to stent 10 of FIGS. 1A–1C, and includes five stent sections 12, 14, 16, 18, 20. Instead of a v-shaped groove for each connecting member 34, 36, 38, 40, however, stent 50 makes use of square grooves 52, 54 56, 58. Specifically, each groove 52, 54, 56, 58 has a substantially square or rectangular cross-section.

As shown in FIG. 2A, each groove 52, 54, 56, 58 extends circumferentially about stent 50 at a position separating two adjacent stent sections 12, 14, 16, 18, 20. Each groove 52, 54, 56, 58 defines a thinned portion of stent 50, weakening the stent to promote breakage. As with stent 10, grooves 52, 54, 56, 58 of stent 50 can be supplemented by perforation, scribing, etching, milling, lathing or other processes to further weaken the respective connecting member 34, 36, 38, 40. Following breakage of connecting members 34, 36, 38, 40, as shown in FIG. 2B, stent sections 12, 14, 16, 18, 20 are free to move relative to one another within the body lumen.

Figure 3A:
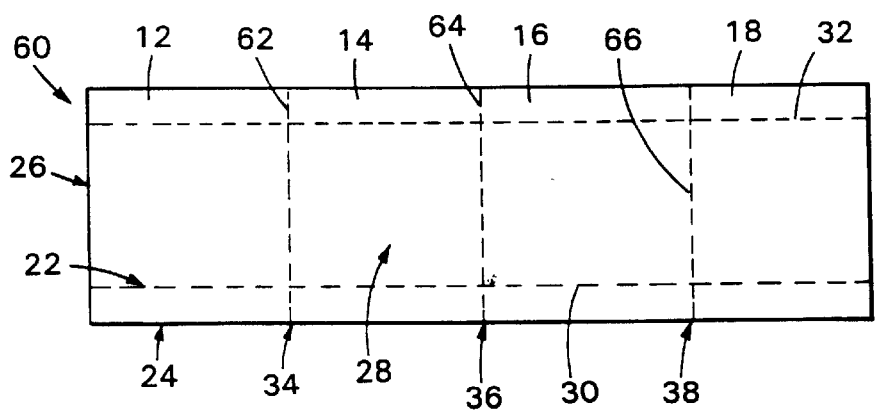
FIGS. 3A and 3B are side views of a multi-section stent having a separable connection structure incorporating perforations.
Figure 3B:
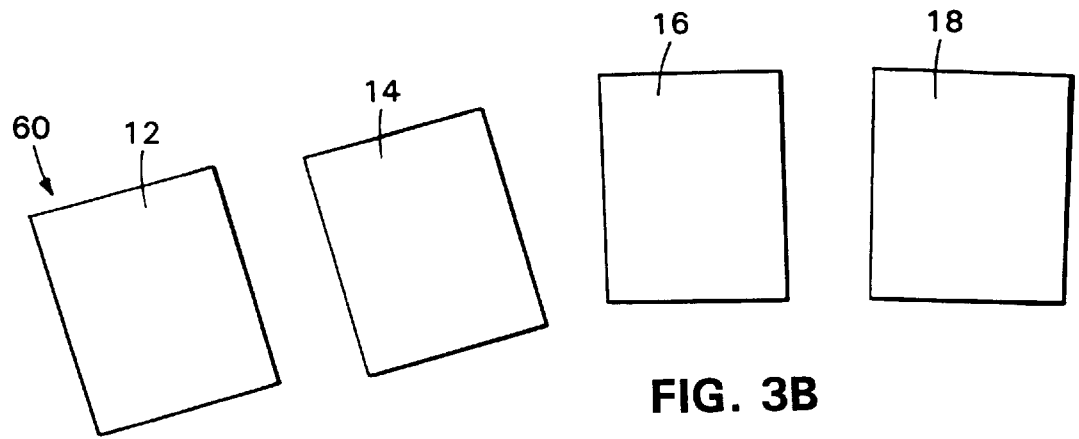

FIGS. 3A and 3B are side views of a multi-section stent 60 having a separable connection structure incorporating perforated connecting members 34, 36, 38, 40. In the example of FIGS. 3A and 3B, stent 60 includes four stent sections 12, 14, 16, 18. Each connecting member 34, 36, 38 is integrally formed with the body of stent 60, but incorporate a series of perforations 62, 64, 66, respectively, that extend about the stent. Each series of perforations 62, 64, 66 defines the junction between adjacent stent sections 12, 14, 16, 18. Perforations 62, 64, 66 weaken stent 60 in the vicinity of the junction, promoting breakage under intraluminal forces.

Perforations 62, 64, 66 can be formed following fabrication of stent 60 by a variety of processes and mechanisms such as, e.g., mechanical needles or punches, laser ablation, or chemical etching. Alternatively, stent 60 could be molded or laminated to yield perforations 62, 64, 66. In some embodiments, it is conceivable that perforations 62, 64, 66 need not extend entirely through the wall of stent 60. Instead, partial penetration of the wall at a series of positions may be sufficient to weaken connecting members 34, 36, 38 for breakage.

Figure 4C:
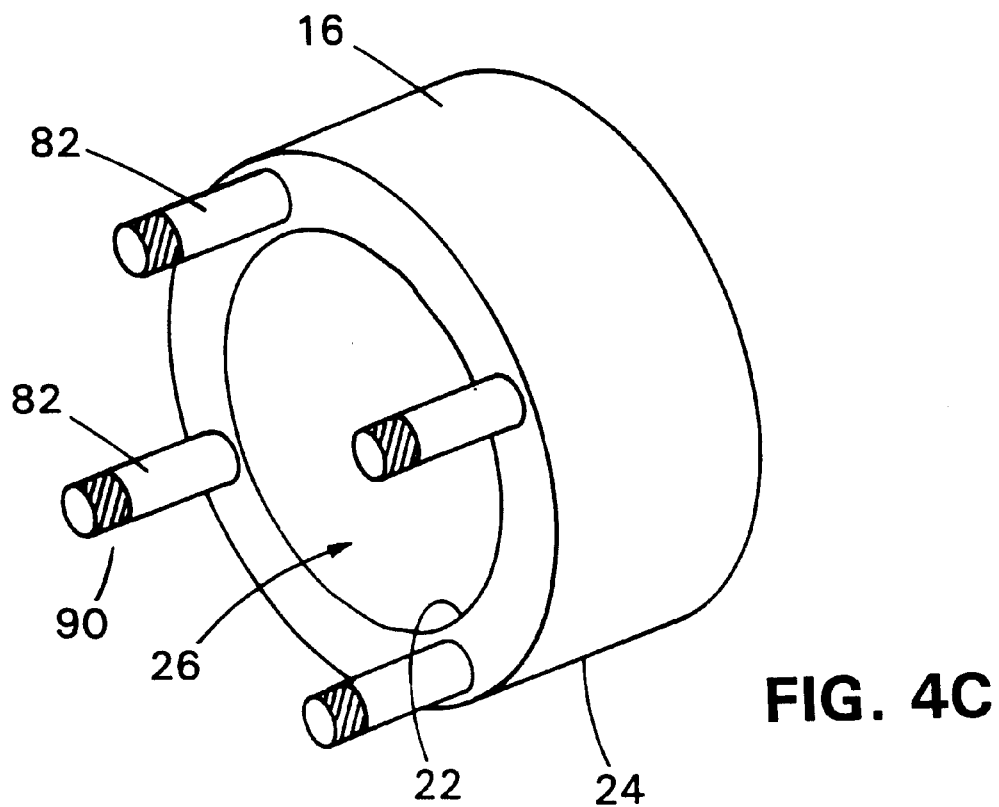
FIG. 4C is a perspective view of a multi-section stent as shown in FIG. 4A.
Figure 4A:
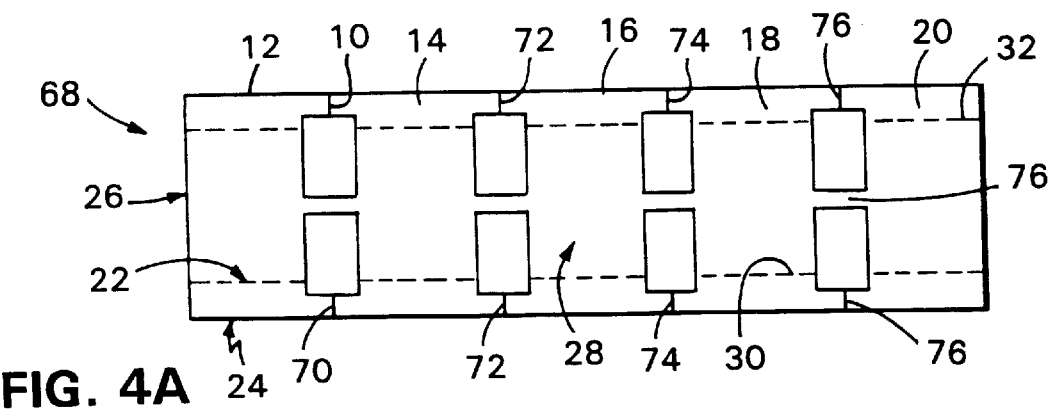
FIGS. 4A and 4B are side views of a multi-section stent having a separable connection structure incorporating discrete breakable connecting members.
Figure 4B:
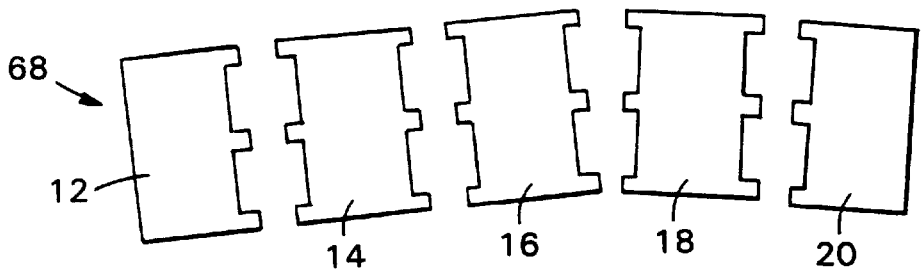

FIGS. 4A and 4B are side views of a multi-section stent 68 having a separable connection structure incorporating sets of discrete breakable connecting members 70, 72, 74, 76. FIG. 4C is a perspective view of multi-section stent 68. As best shown in FIG. 4C, connecting members 70, 72, 74, 76 may form rod-like elements distributed about the periphery of respective stent sections 12, 14, 16, 18, 20 on a side facing adjacent stent sections. Connecting members 70, 72, 74, 76 bridge adjacent stent sections 12, 14, 16, 18 to connect the stent sections and hold stent 68 intact for deployment and positioning within the body lumen.

Each connecting member 70, 72, 74, 76 is manufactured to break under intraluminal forces, however, following deployment of stent 68 within the body lumen. For example, each connecting member 70, 72, 74, 76 may include a weakened portion 78 that promotes breakage. As in other embodiments, weakened portion 78 can be formed by thinning, perforating, or prestressing connecting members 70, 72, 74, 76. Alternatively, stent 68 can be molded to form connecting members 70, 72, 74, 76, along with weakened portions 78. Following breakage of connecting members 70, 72, 74, 76, stent sections 12, 14, 16, 18, 20 are able to move independently, as indicated in FIG. 4B.

Use of rod-like elements as connecting members 70, 72, 74, 76 can provide the added benefit of stability to stent sections 12, 14, 16, 18. In particular, the rod-like elements extend outward from stent sections 12, 14, 16, 18 and can engage the inner wall of the body lumen to resist axial tumbling of the respective stent section. For added stability, connecting members 70, 72, 74, 76 may take the form of tab-like elements that, relative to rod-like elements, exhibit greater lateral surface area for contact with the lumen wall. In either case, the resulting connecting members 70, 72, 74, 76 provide extensions that counteract tumbling forces.

Figure 5A:
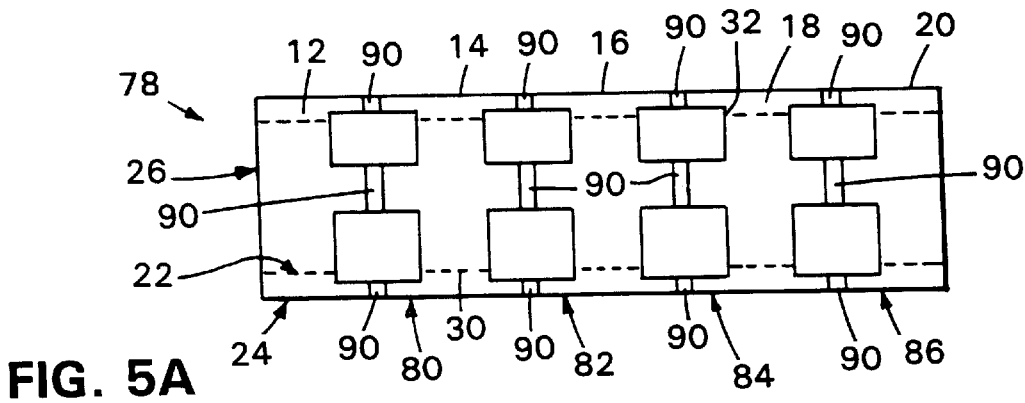
FIGS. 5A and 5B are side views of a multi-section stent having a separable connection structure incorporating discrete breakable connecting members.
Figure 5B:
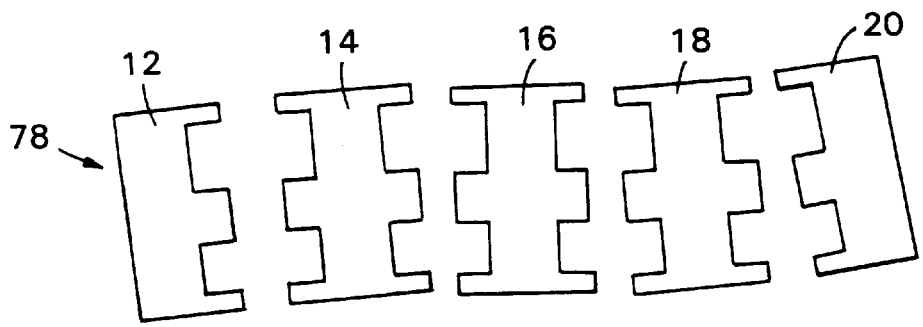

FIGS. 5A and 5B are side views of a multi-section stent 78 having a separable connection structure incorporating sets of discrete degradable or physically breakable connecting members 80, 82, 84, 86. As in stent 68, connecting members 80, 82, 84, 86 may take the form of rod-like, or tab-like elements that bridge a gap between adjacent stent sections 12, 14, 16, 18, 20. In the example of FIGS. 5A and 5B, connecting members 80, 82, 84, 86 take on a tab-like configuration. Connecting members 80, 82, 84, 86 thereby connect stent sections 12, 14, 16, 18, 20 and hold stent 78 intact for deployment and positioning. Each connecting member 80, 82, 84, 86 forms two halves, however, that can be held together with a material 90 that can be made from biodegradable or physically breakable material.

If made with a biodegradable material, material 90 dissolves or otherwise degrades upon interaction with fluids within the body lumen to a point at which connecting members 80, 82, 84, 86 break apart. Alternatively, if made with a physically breakable material, intraluminal forces cause connecting members 80, 82, 84, 86 to break apart at material 90. In this case, the biocompatible material forming material 90 could take the form of a briffle material that is not necessarily degradable, but which readily breaks under intraluminal forces or upon expansion of stent 68. Degradation or physical breakage yields discrete stent sections 12, 14, 16, 18, which then are independently movable within the body lumen.

In the example of FIGS. 5A and 5B, stent sections 12, 14, 16, 18, 20 can be fabricated as discrete components, e.g., by molding, machining, lamination, or other techniques, and bonded together using material 90. In this case, discrete stent sections 12, 14, 16, 18, 20 are connected together to form stent 78. Alternatively, stent 78 could be molded as an integral component, with material 90 being insert molded to connect adjacent connecting members 80, 82, 84, 86. Examples of degradable materials suitable for use as material 90 include fibrin, collagen, polymers, polyurethane, sugars, polyunhydrides, and polyethyloxides. Degradable materials could be mixed with therapeutic substances, if desired, for release into the body lumen upon degradation of material 90. Examples of breakable, biocompatible materials that could be used as material 90 include metals such as gold, silver, platinum, stainless steel, titanium, tantalum, and Nitinol, as well as any of the biodegradable materials mentioned above, i.e., fibrin, collagen, polymers, polyurethane, sugars, polyunhydrides, and polyethyloxides.

Figure 6A:
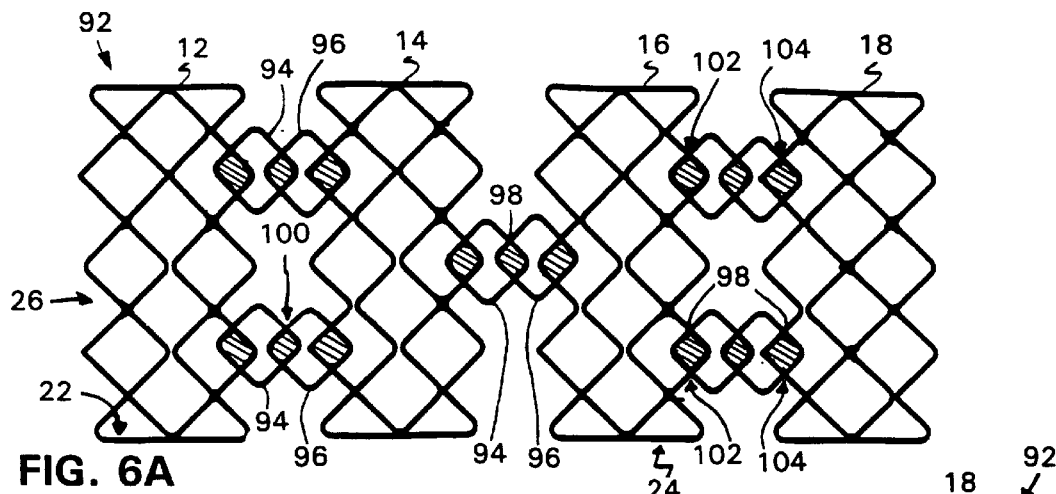
FIGS. 6A, 6B, and 6C are side views of a multi-section stent having a separable connection structure incorporating interlocking links.
Figure 6B:
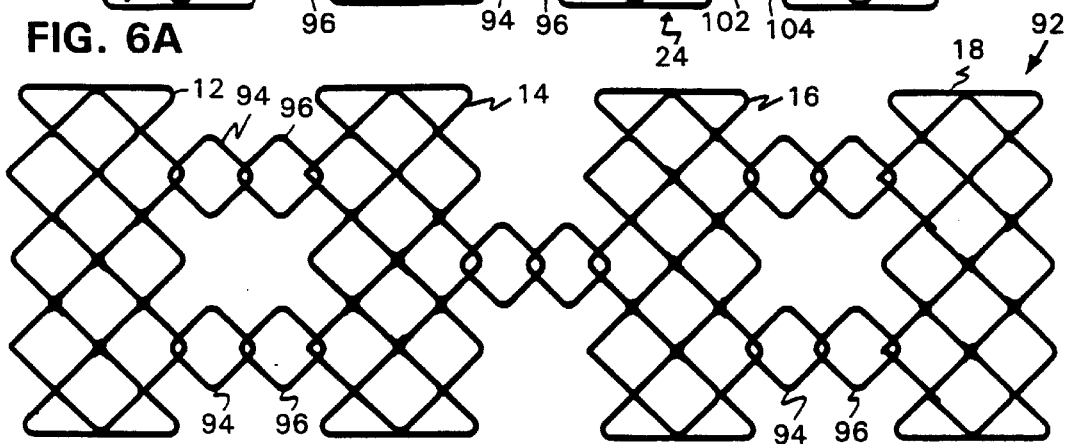
Figure 6C:
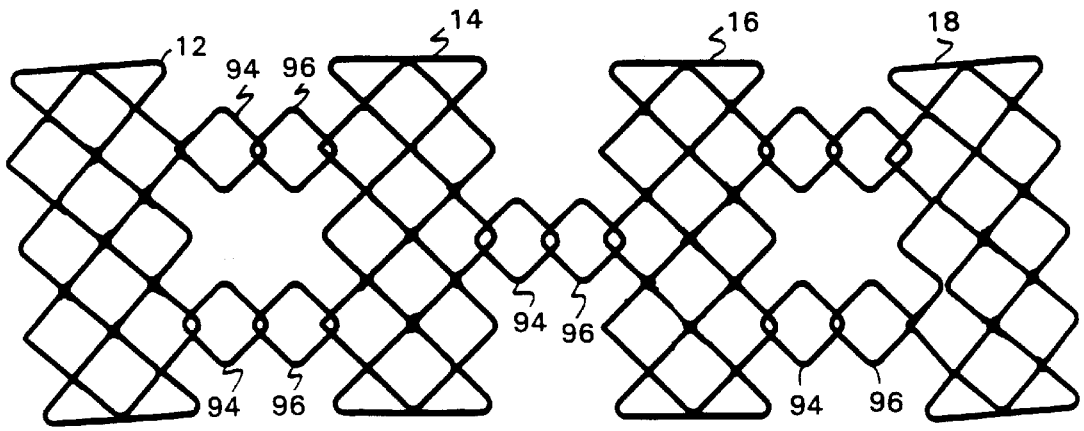

FIGS. 6A, 6B, and 6C are side views of a multi-section stent 92 having a breakable connection structure incorporating pairs of interlocking links 94, 96 that connect adjacent stent sections 12, 14, 16, 18. In the example of FIGS. 6A, 6B, and 6C, each of stent sections 12, 14, 16, 18 takes the form of an interlocking matrix that is woven in a manner similar to a chain link fence. Stent sections 12, 14, 16, 18 in this embodiment can be fabricated from the same materials used for other embodiments. Again, examples of biocompatible materials that could be used include metals such as gold, silver, platinum, stainless steel, titanium, tantalum, and Nitinol. The matrix can be formed from an array of links substantially identical to links 94, 96. The links in each of stent sections 12, 14, 16, 18 define a ring-like structure. Each of links 94, 96 interlocks with a link in one of stent sections 12, 14, 16, 18 at one end, and interlocks with one another at the other end, thereby holding the stent sections together to form stent 92. For example, link 94 extends from a first stent section 12, whereas link 96 extends from a second stent section 14. Link pairs 94, 96 can be distributed about the circumferences of adjacent stent sections 12, 14, 16, 18, holding them at multiple points.

As shown in FIG. 6A, links 94, 96 can be structured to interlock with one another and form an overlap region 100.

Similarly, links 94, 96 may form overlap regions 102, 104 with the stent sections 12, 14, 16, 18 with which they interlock. A degradable or physically breakable material 98 can be formed in each of overlap regions 100, 102, 104 to fortify the interlock, and thereby maintain stent sections 12, 14, 16, 18 in a substantially fixed manner. Thus, the degradable material helps keep multi-section stent 92 intact for deployment and positioning. Also, the degradable material 98 prevents longitudinal movement of stent sections 12, 14, 16, 18 relative to one another, maintaining the stent sections at a predetermined spacing. Following deployment, however, the material degrades, relaxing the interlock between links 94, 96, as well as the interlocks between the links and respective stent sections 12, 14, 16, 18.

Upon degradation of the material in overlap regions 100, 102, 104, stent sections 12, 14, 16, 18 remain connected to one another, but are able to more freely move about the interconnection points. As shown in FIG. 6C, for example, stent sections 12, 14, 16, 18 are able to tilt relative to one another. Notably, in the absence of overlap regions 100, 102, 104, stent sections 12, 14, 16, 18 are able to move longitudinally away from one another, at least to the extent permitted by the remaining interlock points. Consequently, as indicated in both FIG. 6B and FIG. 6C, stent 92 is actually capable of expanding its length following deployment. At the same time, however, the length of stent 92 is constrained by the remaining interconnection of links 92, 94.

Figure 7A:
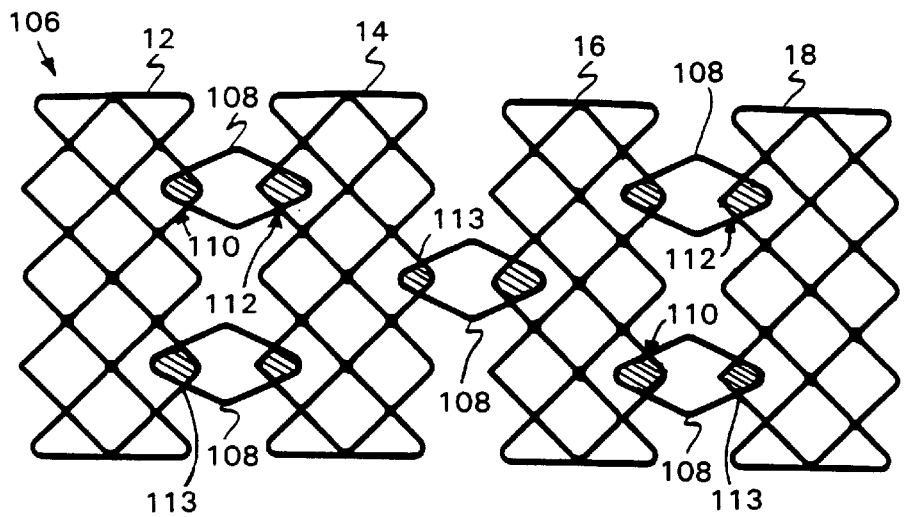
FIGS. 7A and 7B are side views of another multi-section stent having a separable connection structure incorporating interlocking links.
Figure 7B:
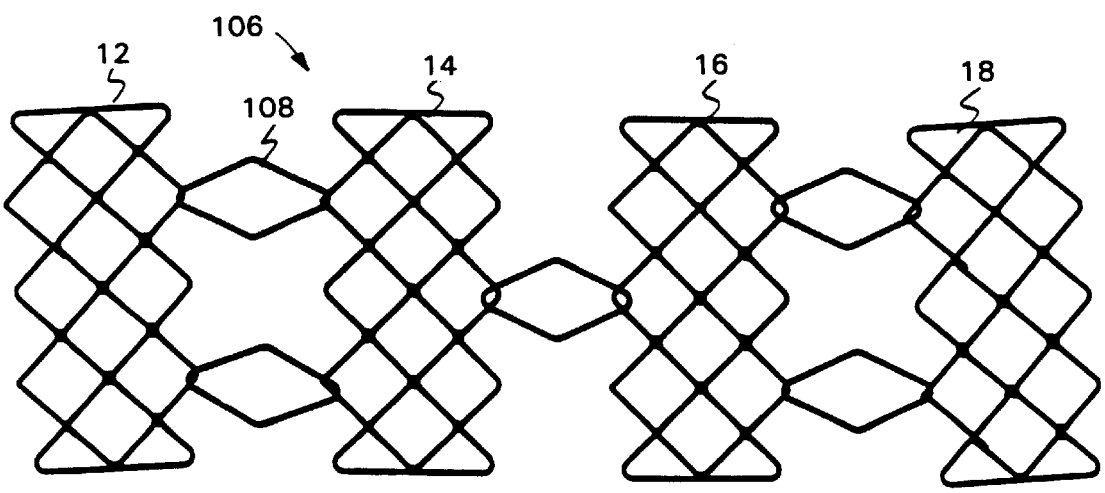

FIGS. 7A and 7B are side views of a multi-section stent 106 having a breakable connection structure incorporating alternative interlocking links 108. Stent 106 conforms substantially to stent 92 of FIGS. 6A–6C. However, stent 106 makes use of a single link 108, instead of link pairs 92, 94, to connect adjacent stent sections 12, 14, 16, 18. Link 108 interlocks with adjacent stent sections 12, 14, 16, 18 at opposite ends, forming overlap regions 110, 112 that can be filled with a breakable or degradable material 113 to fortify the interconnection. As shown in FIG. 7B, following degradation of the material, stent sections 12, 14, 16, 18 are more freely movable. Moreover, upon elimination of overlap regions 110, 112, the length of stent 106 can be expanded.

Figure 8A:
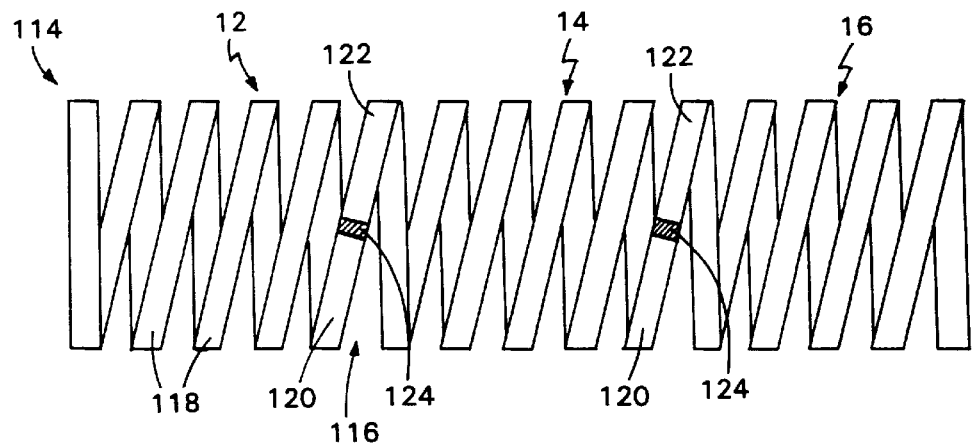
FIGS. 8A and 8B are side views of a multi-section stent having a spring coil structure with separable connecting members.
Figure 8B:
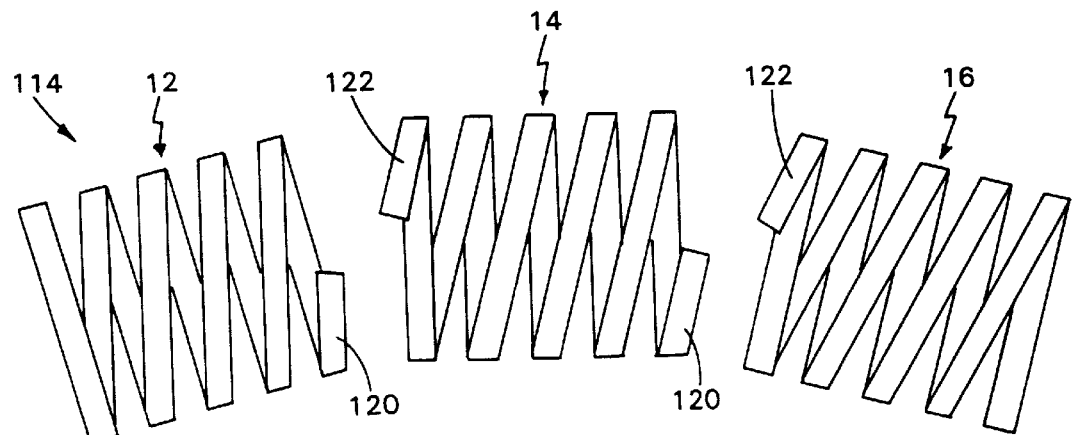

FIGS. 8A and 8B are side views of a multi-section stent 114 having a spring structure with breakable or degradable spring arms 116. Each stent section 12, 14, 16 takes the form of a self-expandable spring coil having multiple turns 118. Spring arms 120, 122 extend between adjacent stent sections 12, 14, 16 to form connecting members. A biodegradable or breakable material 124 joins spring arms 120, 122 to hold stent 114 together. Alternatively, spring arms 120, 122 may form a continuous member that is weakened, e.g., by thinning, perforation, etc., to promote breakage under intraluminal forces. Following breakage, as shown in FIG. 8B, stent sections 12, 14, 16 are detached and freely movable relative to one another.

Figure 9A:
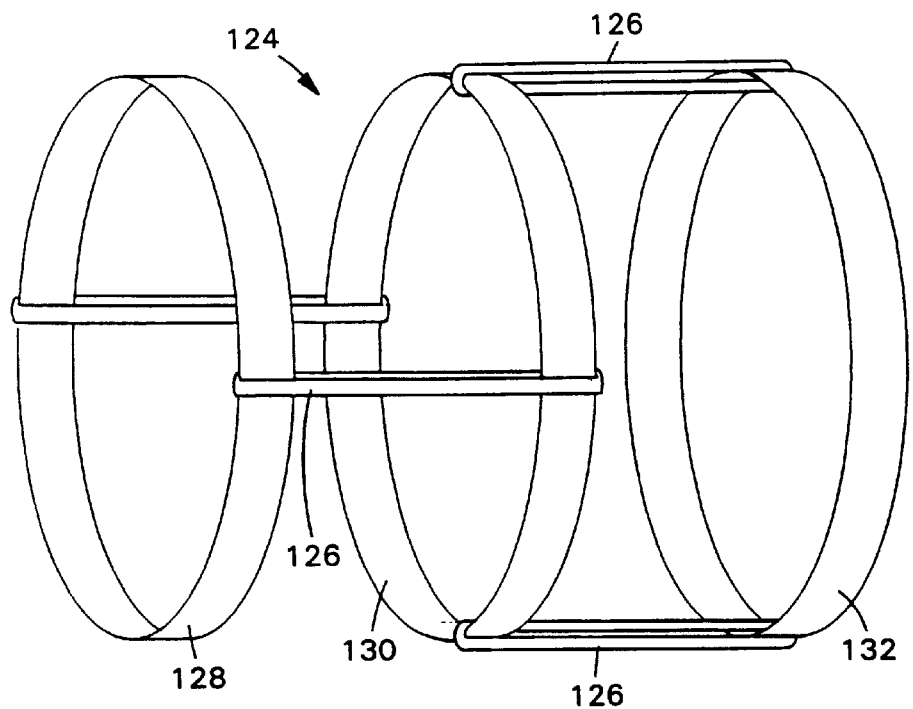
FIGS. 9A and 9B are perspective side views of a multi-section stent with connecting loops.
Figure 9B:
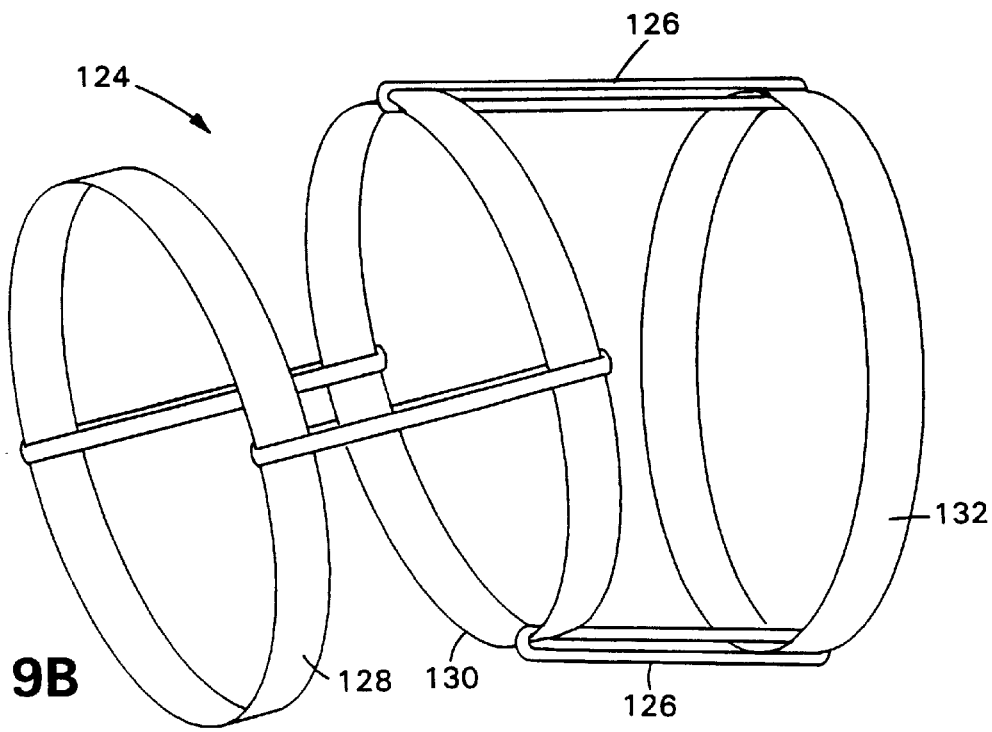

FIGS. 9A and 9B are perspective side views of a multi-section stent 124 having connecting loops 126 that permit movement and flexibility of stent sections 128, 130, 132 relative to one another. As shown in FIG. 9A, each section 128, 130, 132 of stent 124 may take the form of a ring. Adjacent rings 128, 130, 132 are held together by connecting loops 126. Loops 126 can be made from a rigid material and sized to allow play between rings 128, 130, 132. In other words, loops 126 can be sized to permit rings 128, 130, 132 to move back and forth in a longitudinal or tilting direction relative to one another. Loops 126 preferably are sized small enough to limit axial tumbling of rings 128, 130, 132 within the body lumen. Following deployment, rings 128, 130, 132 are movable relative to one another. As a further alternative, loops 126 can be fabricated from an elastomeric material that allows rings 128, 130, 132. In either case, stent 124 provides flexibility, allowing rings 128, 130, 132 to adapt to the body lumen in which the stent is positioned.

Figure 10A:
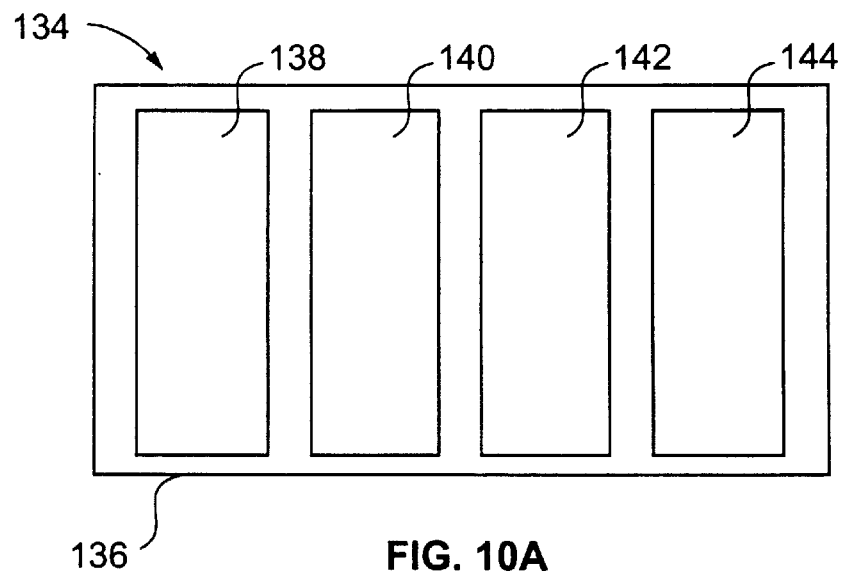
FIGS. 10A and 10C are side views of a multi-section stent with a degradable housing.
Figure 10B:
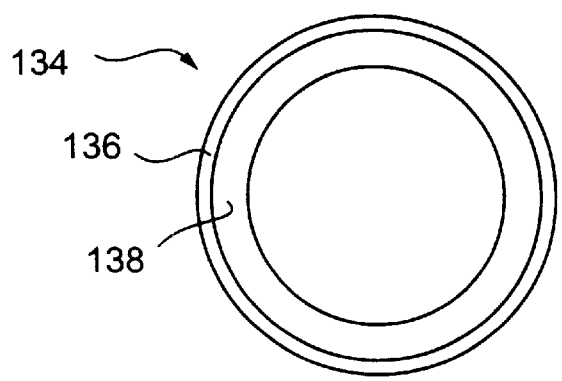
FIG. 10B is an end view of the multi-section stent of FIG. 10A.
Figure 10C:
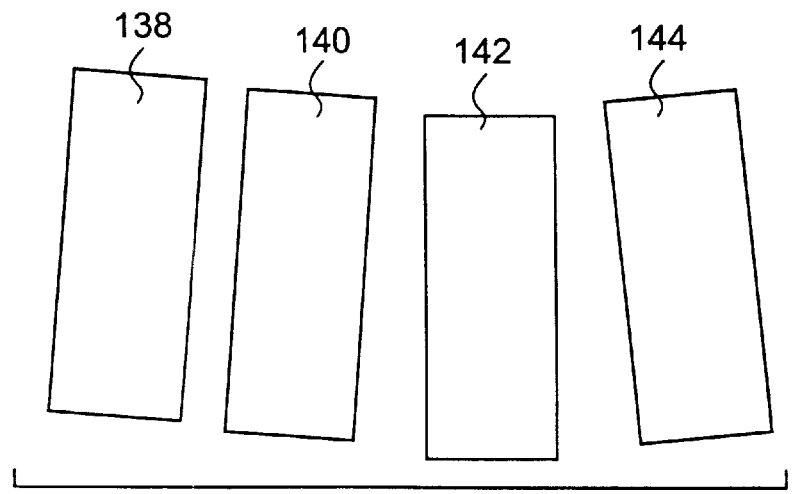

FIGS. 10A and 10C are side views of a multi-section stent 134 having a connecting structure in the form of a degradable housing 136 that binds stent sections 138, 140, 142, 144 together. FIG. 10B is an end view of stent 134. Upon deployment, housing 136 is degradable, thereby releasing sections 138, 140, 142, 144, and allowing them to move relative to one another. As shown in FIG. 10A, housing 136 may take the form of a continuous cylinder that is molded or formed from a sheet. Alternatively, housing 136 may be cage- or net-like, having a number of different threads that cross one another. In either case, housing 136 can be formed from any of the biodegradable materials described herein. Following degradation of housing 136, stent sections 138, 140, 142, 144 are free to move and adapt to the body lumen in which stent 134 is positioned.

Figure 11A:
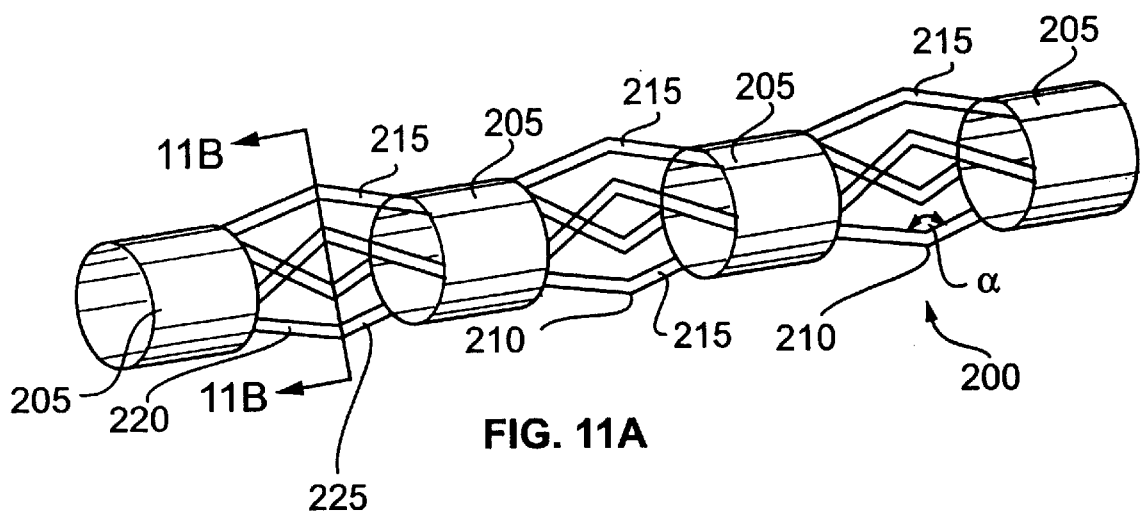
FIG. 11A is a perspective side view of a multi-sectional stent.
Figure 11B:
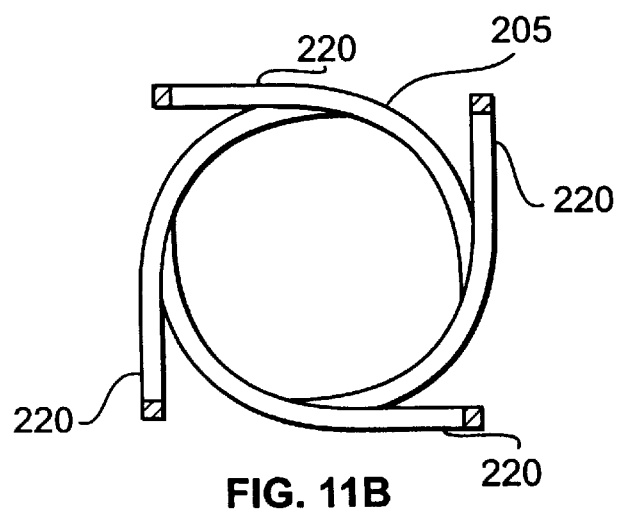
FIGS. 11B and C are an end view and an enlarged side view of the multi-sectional stent of FIG. 11A.
Figure 11C:
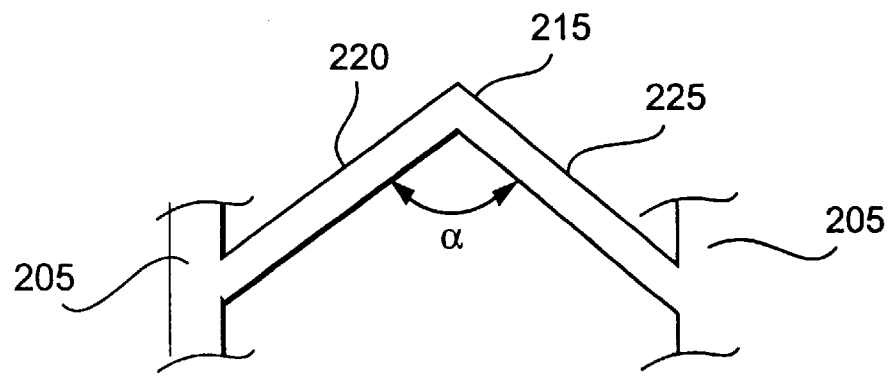
Figure 12:
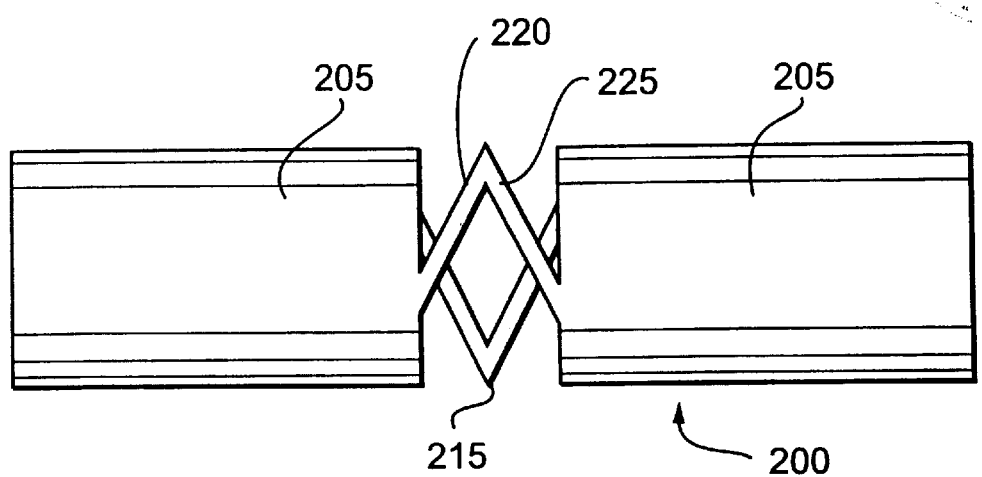
FIG. 12 is a side view of a multi-sectional stent having an angled connecting member in which the angle is relatively small.
Figure 13:
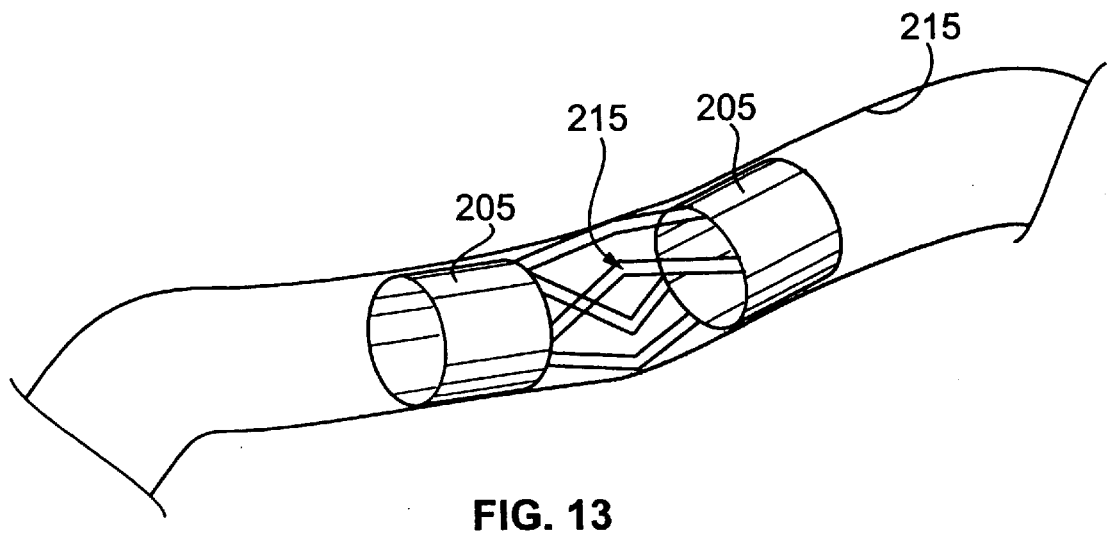
FIG. 13 is a side view of the multi-sectional stent of FIG. 12 deployed in an artery.

FIG. 11A is a perspective view of a multi-sectional stent. FIGS. 11B and C are end and enlarged side views of a multi-sectional stent 200. The multi-sectional stent 200 includes stent sections 205 and a separable connection structure 210 incorporating four sets of discrete, physically breakable connecting members 215 positioned between each pair of stent section 205. The connecting members 215 take the form of a pair connected rods 220 and 225 that form an angle, alpha, at their vertex 230. The angle alpha can be adjusted to increase the lateral and longitudinal flexibility of the stent 200. For example, referring to FIGS. 12 and 13, which are a side view of the multi-sectional stent and the stent deployed in an artery, the angle alpha may be relatively small, e.g., less than 45°. Although the stent 200 may include one or more stent sections 205, for simplicity, only two stent sections are illustrated. In addition, although one or more connecting members 215 can be used to connect adjacent stent sections 205, for simplicity only two connecting members are illustrated. A stent as described above will have good axial flexibility combined with an ability to provide a concentrated opening force along a relatively short length of an artery 235 because the stent sections 205 are deployed close to each other.

Figure 14:
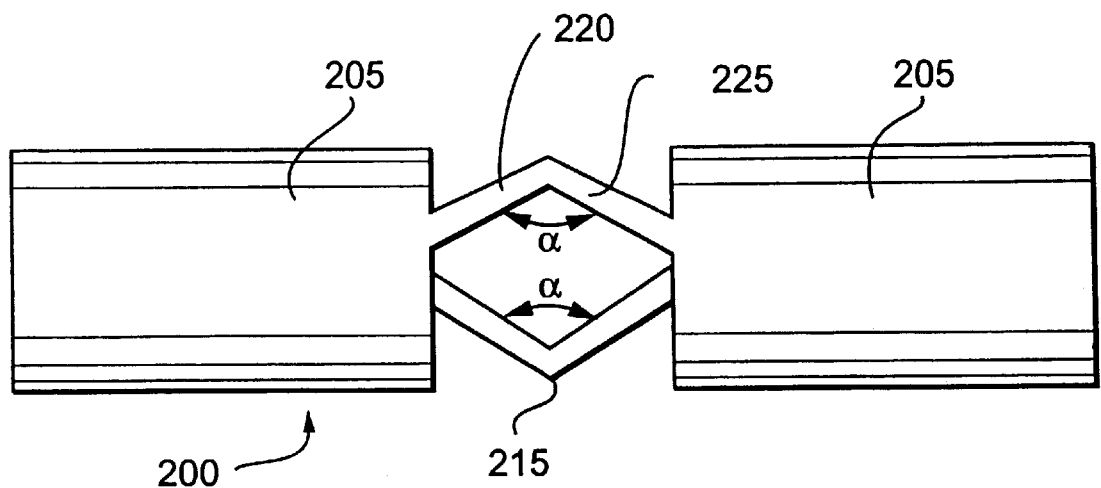
FIG. 14 is a side view of a multi-sectional stent having an angled connecting member in which the angle is relatively large.
Figure 15:
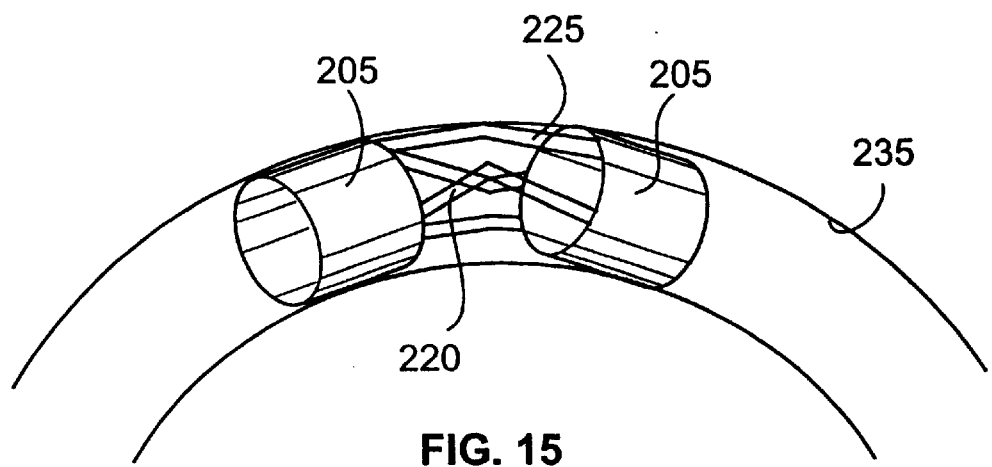
FIG. 15 is a side view of the multi-sectional stent of FIG. 14 deployed in an artery.
Figure 16:
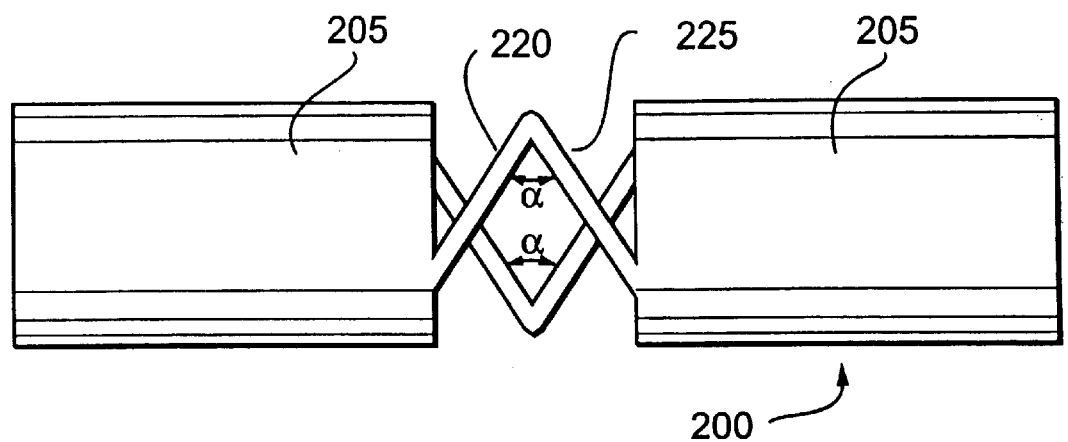
FIG. 16 is a side view of a multi-sectional stent having an angled connecting member.

Referring to FIGS. 14 and 15, which show a side view of the multi-sectional stent having a relatively large angle and the stent deployed in an artery, the angle alpha may be relatively large, e.g., greater than 135°. Such a connecting member configuration will provide good lateral flexibility, i.e., the ability to be delivered through tortuous vessels, combined with an ability to provide an opening force separated over a relatively long length of the artery 235. Referring to FIG. 16, the angle alpha may be in a middle range, i.e., between 45° and 135°, such as an angle of 90°. Such a connecting member configuration will provide moderate lateral flexibility and moderate axial flexibility combined with an ability to provide an opening force separated over a length of the artery 235.

Figure 17:
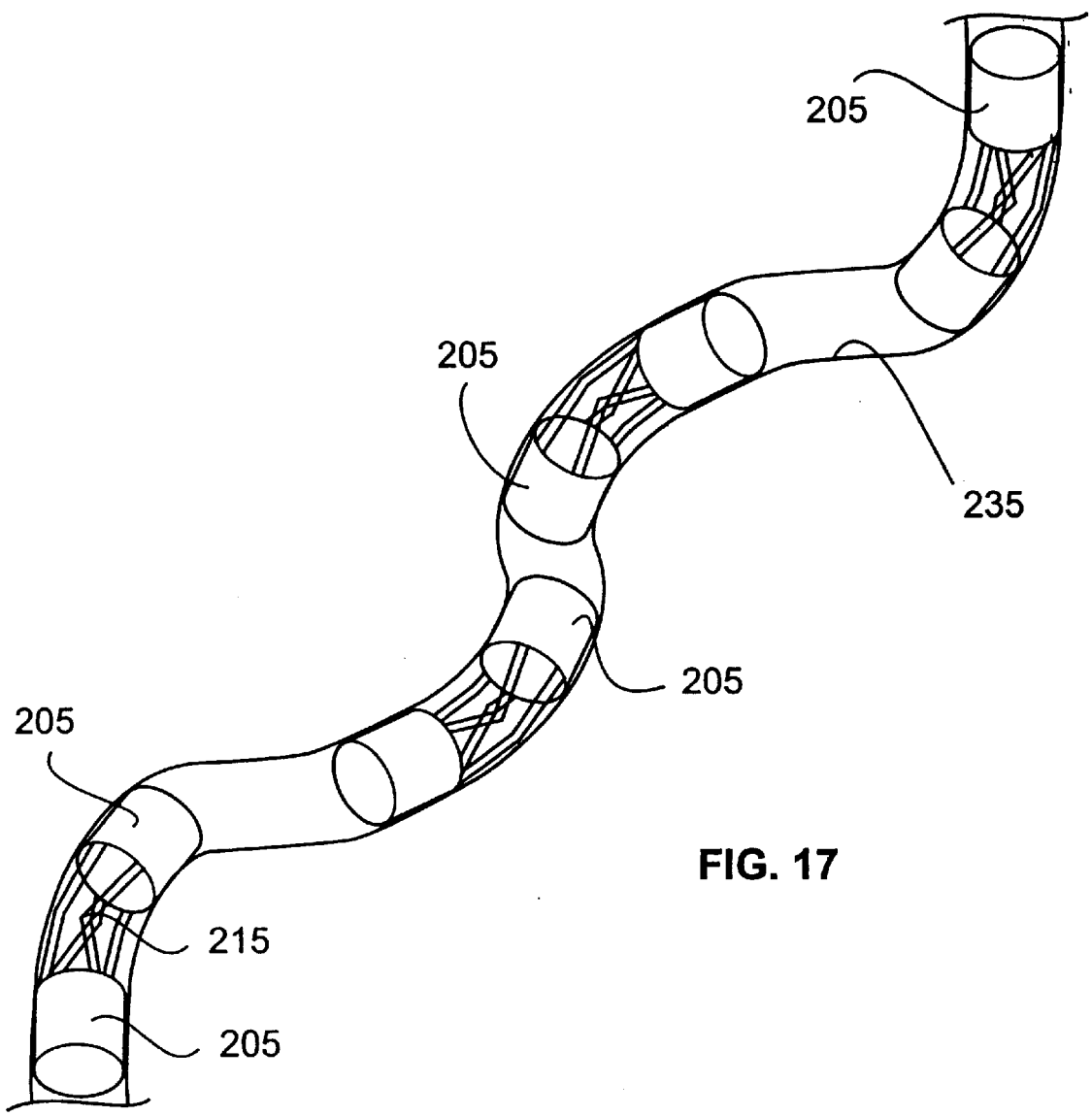
FIG. 17 is a side view of a multi-sectional stent deployed in a tortuous artery.

The angle alpha can be specified based upon the patient's particular vasculature and the characteristics of the lesion being treated. Moreover, the number of the stent sections 205 can be varied for the same reasons. For example, referring to FIG. 17, which shows a deployed stent in a tortuous artery, a patient having tortuous arteries with lengthy regions of severe lesions 240 may be treated with multiple multi-sectional stents 200, each having two stent sections 205 joined by connecting members 215 having the angle alpha formed relatively small. The stents 200 are deployed adjacent to other stents 200 so that together they provide a concentrated opening force in the lumen of the artery 235 along a long length of the artery. The reduced number of stent sections 205 in each stent 200 improves the ability of a cardiologist or radiologist to deploy the stents through and in tortuous vessels. The magnitude of the angle alpha causes the stent sections 205 to be closely adjacent to and supportive of the lumen of the artery 234.

Referring to FIG. 18, a patient having less torturous arteries 235 but nonetheless having severe lesions 245 would need an opening force concentrated along a considerable length of the artery. The stent 200 to treat such a patient has a greater number of stent section 205 with a relatively small angle alpha. Although not as flexible along its length, the stent 200 can be delivered to the lesions along a greater length of the artery 235 than can the stent 200 of FIG. 17.

Modifications can be made to the multi-sectional stent 200 beyond those described above. For example, referring to FIGS. 19 and 20, the number and length of the breakable connecting members can be varied. Specifically, referring to FIG. 19, the multi-sectional stent 200 includes one connecting member 215 that connects adjacent stent section 205. The length of the connecting members 215 can be varied along the length of the stent 200 to tailor the stent's characteristics, such as flexibility, to a patient's vasculature and disease condition. Referring to FIG. 20, the stent sections 205 are connected by pairs of connecting members 215 connected substantially adjacent to each other along the circumference of the stent section. By connecting the connecting member 215 to the stent section 205 in this manner the stent has increased flexibility because the flex points are close to each other. Such a configuration is easily deployed through tortuous vessels.

Figure 21:
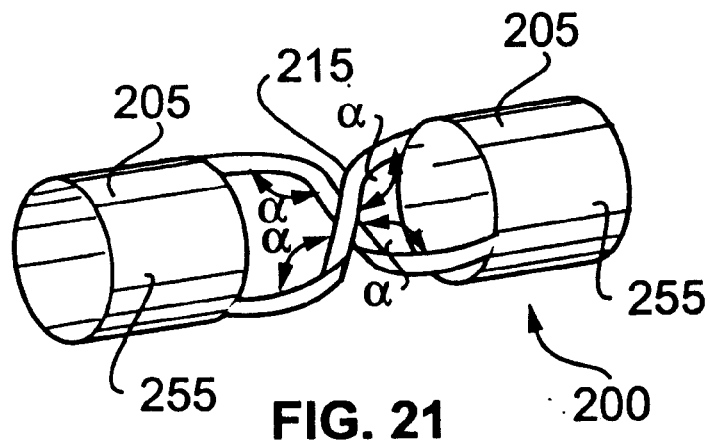
FIG. 21 is a perspective view of a multi-sectional stent having angled connecting members attached at offset positions.
Figure 22:
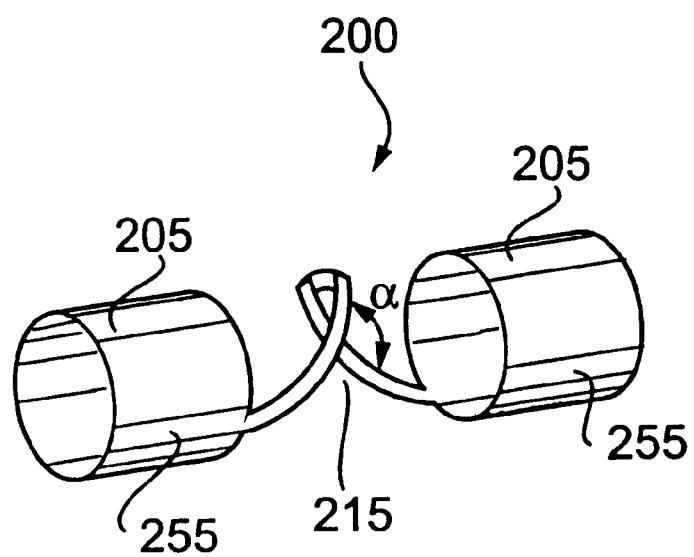
FIG. 22 is a perspective view of a multi-sectional stent having an angled connecting member attached at offset positions.

Although stent 200 is shown above with the connecting members 215 attached to adjacent stent section 205 at analogous locations around the circumference of the adjacent stent sections, the connecting member 215 can be attached at offset points around the circumference of the stent sections. For example, as illustrated in FIGS. 21 and 22, the connecting members 215 are attached at positions that are approximately 180° offset along the circumference of adjacent stent section 205. The connecting members 215 may be in the same plane as an outer wall 255 of the stent sections 205. In this configuration, the connecting members 215 curve around the plane of the circumference of an outer surface 255 of the stent sections 205. The stent 200 of FIG. 21 has two connecting members 215 connecting the stent sections 205. The connecting members 215 are each formed with a pair of angles alpha, and the vertex of each angle being closer to the stent sections that shown in the implementations described above.

In the stent of FIG. 22, the vertex of the angle alpha is centered between the adjacent stent sections 205. Although the connecting member 215 is illustrated as encircling approximately 300° of the circumference of the stent sections 205, that characteristic can be varied more or less. For example, the connecting member 215 may encircle two circumferences, i.e., 720°, and have an angle alpha with a vertex formed at a point that is approximately halfway through that 720° encirclement. Such a configuration is very flexible and can be used to connect multiple stent sections 205 to be placed in a long section of the artery.

The stent 200 may be deployed and positioned in an artery by, for example, balloon expansion or using the inherent expansion property of the material, such as Nitinol, of which the stent sections 205 and connecting members 215 are constructed. If balloon expansion using a balloon catheter is the method used for delivering the stent 200, the stent first is placed over the balloon so that it can be delivered to the lesion at which it will be expanded. Because of the wide variation in stent configurations, as described above, a range of balloon diameters and lengths may be used to match the characteristics of the stent to artery in which the stent will be deployed. For example, to stent large arteries a large diameter balloon should be selected to ensure that the balloon opens the stent completely. Similarly, if the stent is relatively long, the balloon should have a corresponding length to ensure that the entire length of the stent is expanded. Although the stents and balloons may be supplied separately to the physician, a manufacturer may provide a selection of kits containing a combination of a stent and a properly sized balloon catheter mounted to the stent. The kit also may contain other devices necessary for the procedure of deploying the stent, such as an introducer, guide wire, scalpel, and sutures.

If the stent is made of a material with shape memory characteristics, such as Nitinol, the stent may be deployed on a catheter and surrounded by a sheath that prevents the stent from expanding. When the stent is positioned in the lumen of the artery adjacent to the lesion, the sheath is removed and the stent expands to open the lumen of the artery. Because of the wide variation in stent configuration, a range of sheaths may be available for matching with the particular stent.

Figure 23:
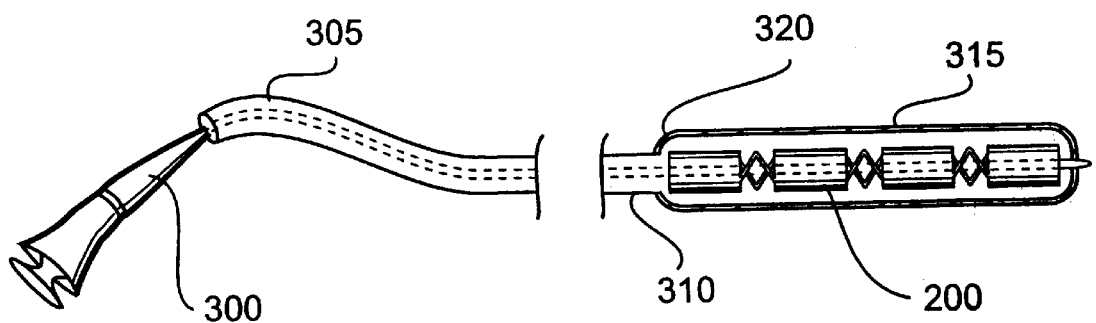
FIGS. 23 and 24 are perspective views of a catheter having a sheath for deploying a stent fabricated from a shape memory material.
Figure 24:
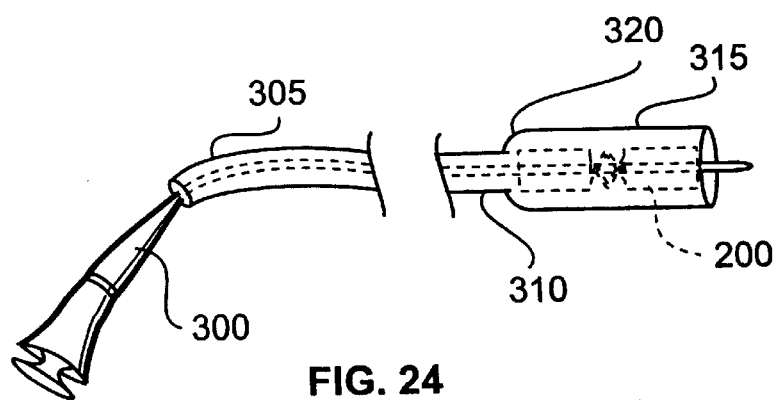

Referring to FIGS. 23 and 24, a catheter 300 for delivering a stent made of a shape memory metal includes a sheath 305 for surrounding the stent to be delivered. The sheath 305 includes a first diameter section 310 and a second diameter section 315. The stent is surrounded by the second diameter section 315, which, as illustrated, has a greater inner diameter than does the first diameter section 310. A shoulder 320 defined at the intersection of the two sections 310, 315 prevents the stent 300 from sliding proximally along the catheter 300. As illustrated in FIG. 23, the length of the second section 315 can be relatively long, or, as illustrated in FIG. 24, relatively short. Other variations in the relative length of the sections 310, 315 are possible and may be selected based on the configuration of the stent 200 and the vasculature in which the stent will be deployed and positioned.

When the stent 200 is deployed in an artery, the connecting members 215 may physically separate from one of the adjacent stent sections 205. The physical separation also may occur at a later time by enzymatic action, dissolution of a coating on the connecting member, the pulsatile movement and forces imparted by the artery surrounding the stent sections, or one of the other means described above. To control the physical separation more predictably, the connecting member 215 may be weakened so that it will break preferentially at a particular location, for example, at the vertex of the angle alpha of the two rods 220, 225, or at their connections to the stent sections 205. The force exerted on the stent when it is expanded by the balloon, or by the stent itself when it expands due to shape memory properties, may be sufficient to cause the connecting members 215 to break from the stent sections. Referring to the stent 200 of FIGS. 21 and 22, the attachment of the connecting members 215 to the stent sections 205 will be stressed as the stent sections 205 expand or are expanded because the attachments are on opposite sides of the expanding circumferences of the adjacent stent sections 205. Accordingly, in this configuration, the stent sections are physically separated during the deployment of the stent.

In the above configurations, the separated connecting member 215 has an end that is separated from a stent section 205, or the rods 220 and 225 each have an end that is separated from the respective adjacent rod 225, 220. The end, which may be in contact with the inner wall, or intima, of the artery may be formed so that it is smooth or has minimally sharp edges that may otherwise irritate the intima. The end of the connecting member to be separated may be weakened, as described above, and then polished around the weakened portion to smooth any rough or sharp edges. Nonetheless, even if there is a sharp edge remaining after separation, scar tissue will form around the separated connecting member and encapsulate the sharp edge. To encourage tissue formation on the surfaces of the connecting members and stent sections, if desired, the surfaces of those components may be textured to encourage tissue in-growth and the formation of a stable layer of tissue on the surfaces.

Figure 25:
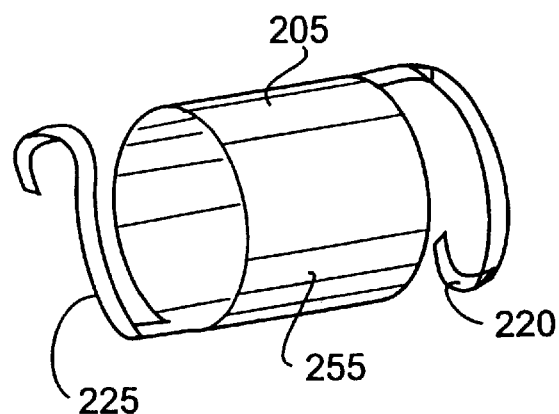
FIGS. 25–27 are perspective views of separated stent sections having attached connecting members.
Figure 26:
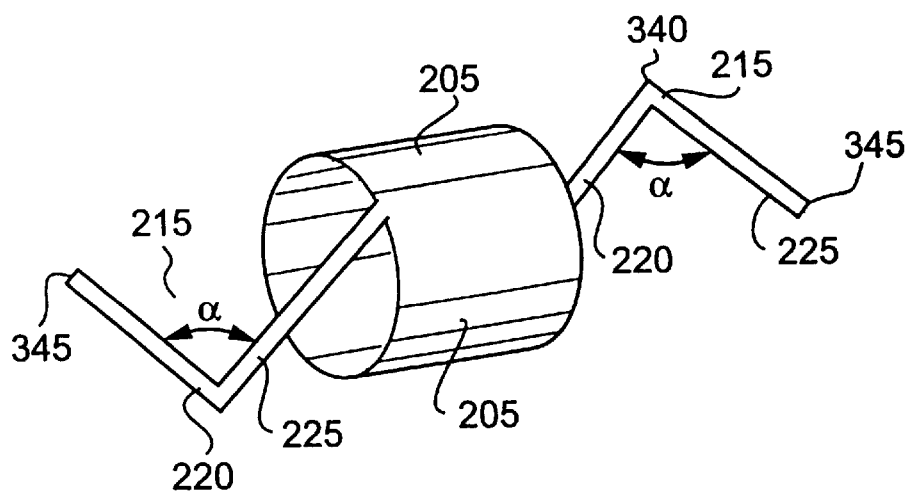
Figure 27:
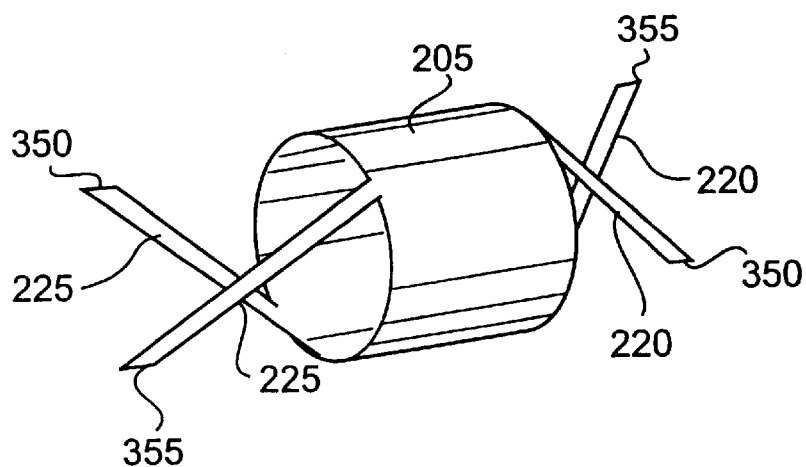
Figure 28:
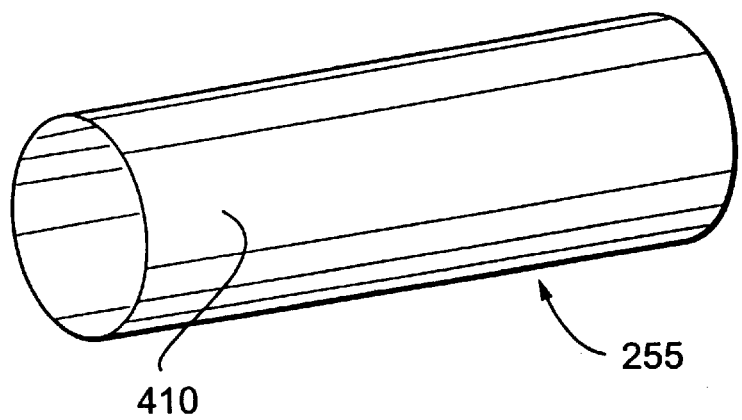
FIGS. 28–31 are perspective view of the steps of forming a multi-sectional stent using electron discharge machining ("EDM").
Figure 29:
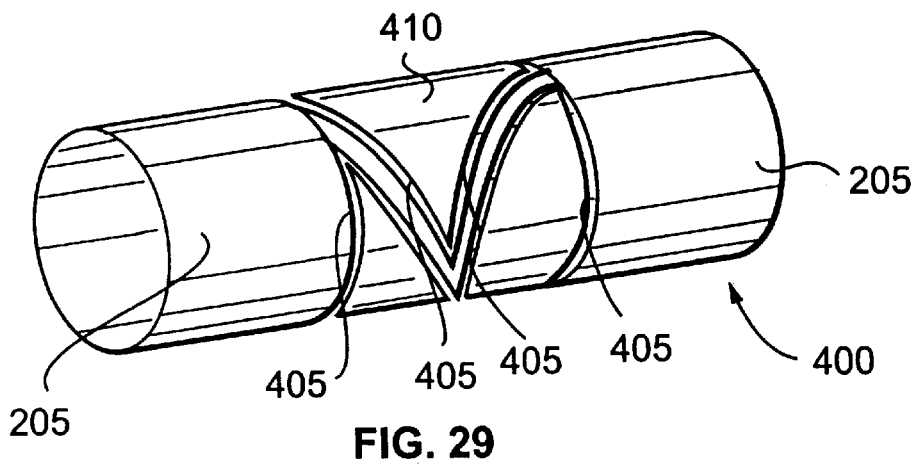
Figure 30:
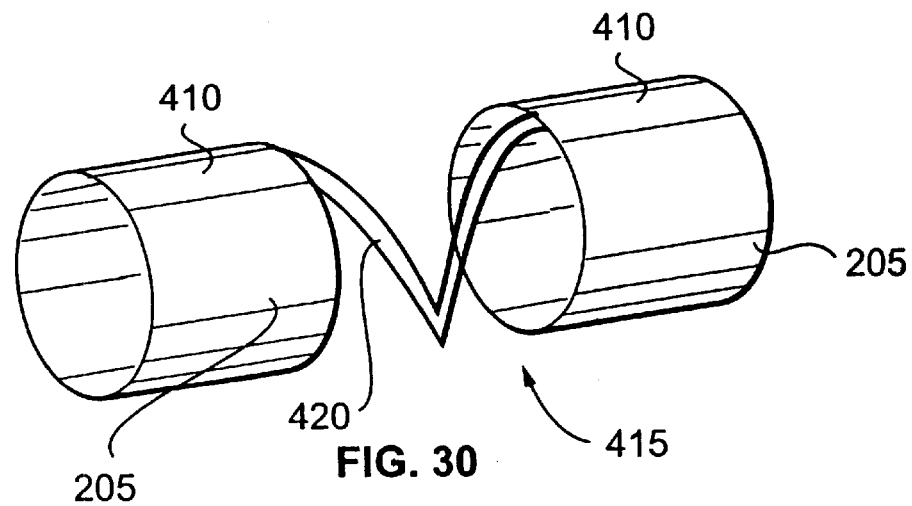
Figure 31:
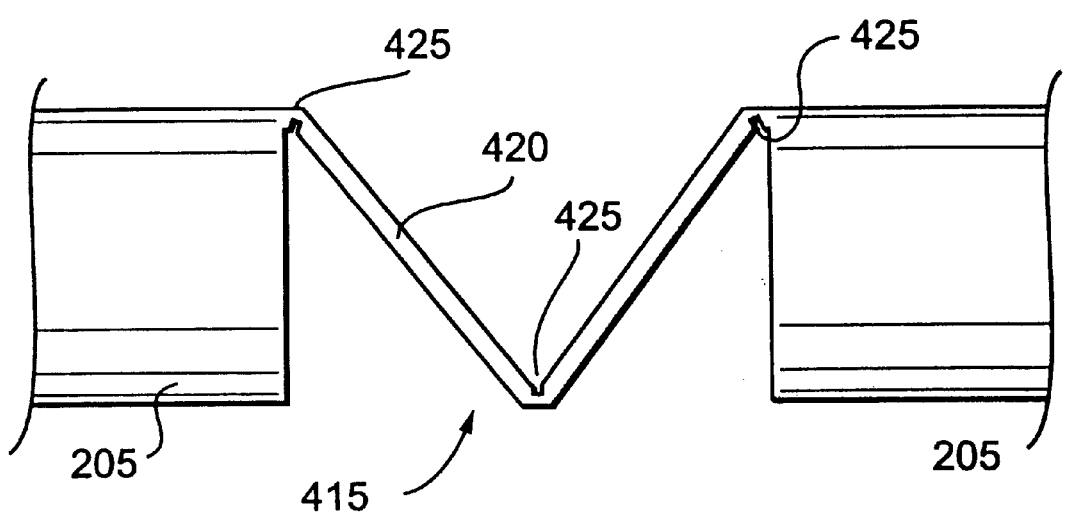

The separated connecting members 215 can provide a stabilizing function for the separated stent sections by acting as leverage against tumbling. Referring to FIGS. 25–27, the stent sections 205 can be separated from the connecting members 215 in a variety of configurations that provide leverage to prevent the stent sections from tumbling within the artery. Each stent section 205, as shown in FIG. 25, may have two attached connecting members 215 that function in combination to prevent tumbling and to stabilize the orientation of the stent section 205. The connecting members 215 are co-planar and follow the circumference of the outer surface 255 of the stent section 205, or are close to being coplanar to the outer surface 255 of the stent section. As the length of the connecting members 215 or the stent sections 205 are increased, and as the distance that the connecting member extends away from the stent section is increased, the likelihood of tumbling is reduced.

The stent sections 205 shown in FIG. 26 are not necessarily co-planar with the connecting members 215 and in contact with the intimal layer of the artery, which would have a tendency to prevent tumbling. Nonetheless, each connecting member has two potential points of contact 340, 345 with the arterial wall to prevent tumbling. One point 345 of the connecting member prevents clockwise tumbling and the other point 340 prevents counter-clockwise tumbling. The stent 200 of FIG. 26 can be modified to have a single connecting member 215 attached and still restrict any tendency of the stent section 205 to tumble.

The stent section 205 shown in FIG. 27 is separated from the adjacent stent sections 205 by breaking or separating two connecting members 215 at the vertex of the angle alpha. Like the stent sections of FIG. 26, two points 350 prevent clockwise tumbling and two different points 355 prevent counter-clockwise tumbling.

These stents can be fabricated using the materials and methods for the various stents described above. In addition, these stents can be fabricated using electron discharge machining ("EDM"). For example, as illustrated in FIGS. 28–31, a tube 400 has a series of slots 405 cut through an outer wall 410. When the series of slots 405 are cut and the cut wall sections are removed, a stent 415 with a connecting member 420 results. Additionally, the stent can have grooves 425 cut into the connecting member 420 to weaken the member so that it will preferentially separate at the predetermined grooves 425. A number of embodiments of the present invention have been described. Nevertheless, it will be understood that various modifications may be made without departing from the spirit and scope of the invention. Accordingly, other embodiments are within the scope of the following claims.

What is claimed is:

1. A stent comprising:

a first stent section;

a second stent section; and at least one connecting member having a first end attached to the first stent section, a second end attached to the second stent section and a physically separable portion.

2. The stent of claim 1, wherein the physically separable portion comprises at least one groove in the connecting member.

3. The stent of claim 2, wherein the groove is formed adjacent to the first end.

4. The stent of claim 2, wherein grooves are formed adjacent to the first end and the second end.

5. The stent of claim 1, wherein the connecting member further includes an angled portion including an angle.

6. The stent of claim 5, wherein the angled portion includes a groove and the physically separable portion comprises the groove.

7. The stent of claim 5, wherein the angle is less than 45°.

8. The stent of claim 5, wherein the angle is between 45° and 135°.

9. The stent of claim 5, wherein the angle is between 135° and 180°.

10. The stent of claim 1, wherein the stent includes four connecting members.

11. The stent of claim 1, wherein the stent includes two connecting members.

12. The stent of claim 1, wherein each connecting member includes a first end attached to the first stent section and a second end attached to the second stent section and the first end of the first stent is adjacent to the first end of the second stent.

13. The stent of claim 12, wherein the first end of the first connecting member and the first end of the second connecting member are separated by approximately 180°.

14. The stent of claim 13, wherein the second end of the first connecting member and the second end of the second connecting member are separated by approximately 180°.

15. The stent of claim 1, wherein the physically separable portion separates during a deployment of the stent.

16. The stent of claim 1, wherein the physically separable portion separates after a deployment of the stent.

17. The stent of claim 1, wherein the stent sections comprise a shape memory material.

18. A stent comprising:

a first stent section;

a second stent section; and a pair of connecting members positioned between the stent sections and connecting the stent sections, wherein each connecting member is substantially co-planar over a portion of a length of the connecting member with the at least one stent section and includes a first end attached to the first stent section, a second end attached to the second stent section and a physically separable portion.

19. The stent of claim 18, wherein the physically separable portion of a first connecting member is configured to separate from the first stent section and the physically separable portion of the second connecting member is configured to separate from the second stent section, whereby the first connecting member is configured to reduce tumbling of the first stent section and the second connecting member is configured to reduce tumbling of the second stent section.

20. The stent of claim 18, wherein the stent is fabricated by electron discharge machining.

* * * * *